US011298112B2

(12) United States Patent
Kashyap et al.

(10) Patent No.: US 11,298,112 B2
(45) Date of Patent: Apr. 12, 2022

(54) BIOMONITORING DEVICES, METHODS, AND SYSTEMS FOR USE IN A BATHROOM SETTING

(71) Applicant: Toi Labs, Inc., San Francisco, CA (US)

(72) Inventors: Vikram Kashyap, San Francisco, CA (US); Kevin D. Simmons, San Francisco, CA (US); Thomas Reidemeister, Waterloo (CA); Benjamin K. Yaffe, San Francisco, CA (US); Rodolfo Camacho, San Francisco, CA (US)

(73) Assignee: TOI LABS, INC., San Francisco, CA (US)

( * ) Notice: Subject to any disclaimer, the term of this patent is extended or adjusted under 35 U.S.C. 154(b) by 0 days.

(21) Appl. No.: 16/446,111

(22) Filed: Jun. 19, 2019

(65) Prior Publication Data
US 2019/0298316 A1 Oct. 3, 2019

Related U.S. Application Data

(63) Continuation of application No. 16/016,559, filed on Jun. 23, 2018, now Pat. No. 10,376,246, which is a
(Continued)

(51) Int. Cl.
*G01N 33/49* (2006.01)
*A61B 10/00* (2006.01)
(Continued)

(52) U.S. Cl.
CPC ........ *A61B 10/0038* (2013.01); *A61B 10/007* (2013.01); *E03D 11/13* (2013.01);
(Continued)

(58) Field of Classification Search
CPC .... E03D 11/13; A61B 10/0038; A61B 10/007
See application file for complete search history.

(56) References Cited

U.S. PATENT DOCUMENTS 7,002,480 B2* 2/2006 Kobayashi ............ B60S 1/0822
250/208.1
2003/0074731 A1* 4/2003 Sumino ................... A47K 13/10
4/667
(Continued)

FOREIGN PATENT DOCUMENTS

| EP | 18780773.0 | 11/2020 | |
| JP | WO2015/1994405 | * 12/2001 | ........... G01N 33/483 |
| WO | WO2016135735 | * 2/2016 | ............ G01N 21/00 |

OTHER PUBLICATIONS

Dongil Lee, "A prototype high sensitivity load cell using single walled carbon nanotube strain gauges", 2012 (Year: 2012).*

*Primary Examiner* — Maurice C Smith
(74) *Attorney, Agent, or Firm* — Elie Gendloff; Gendloff IP

(57) ABSTRACT

Provided is a biomonitoring device that measures a parameter of a material expelled during use of a toilet by a user. Also provided is a biomonitoring mirror device that identifies a user, detects a febrile illness in a user, dispenses medications/supplements, connects to electrical device accessories in the bathroom, and provides an interactive user interface. Additionally provided is a system for measuring a parameter of a material expelled during use of a toilet by a user. Further provided is a method of determining a physiological parameter of a user.

18 Claims, 41 Drawing Sheets

Related U.S. Application Data continuation of application No. PCT/US2018/026618, filed on Apr. 6, 2018.

(60) Provisional application No. 62/482,912, filed on Apr. 7, 2017.

(51) Int. Cl.

| | |
|---|---|
| *G01N 33/483* | (2006.01) |
| *G01N 33/493* | (2006.01) |
| *G01N 21/31* | (2006.01) |
| *H04N 5/33* | (2006.01) |
| *H04N 5/374* | (2011.01) |
| *E03D 11/13* | (2006.01) |

(52) U.S. Cl.
CPC ......... *G01N 21/31* (2013.01); *G01N 33/4833* (2013.01); *G01N 33/49* (2013.01); *G01N 33/493* (2013.01); *H04N 5/332* (2013.01); *H04N 5/374* (2013.01); *A61B 2010/0083* (2013.01)

(56) References Cited

U.S. PATENT DOCUMENTS

| | | | |
|---|---|---|---|
| 2008/0301865 A1* | 12/2008 | Hand | E03D 9/052 4/216 |
| 2009/0216099 A1* | 8/2009 | Kim | G01N 33/493 600/345 |
| 2014/0083780 A1* | 3/2014 | Tsutaya | G01G 3/12 177/211 |
| 2015/0042834 A1* | 2/2015 | Miao | H04N 5/2251 348/218.1 |
| 2015/0060647 A1 | 3/2015 | Sakamoto et al. | |
| 2015/0342574 A1 | 12/2015 | Hall et al. | |
| 2016/0316978 A1* | 11/2016 | Peng | A47K 13/30 |
| 2017/0022536 A1* | 1/2017 | Velazquez | A61B 10/007 |
| 2018/0092602 A1* | 4/2018 | Hall | A47K 13/24 |
| 2018/0255989 A1* | 9/2018 | Kappeli | A47K 13/302 |
| 2020/0008786 A1 | 1/2020 | Sekine | |

\* cited by examiner

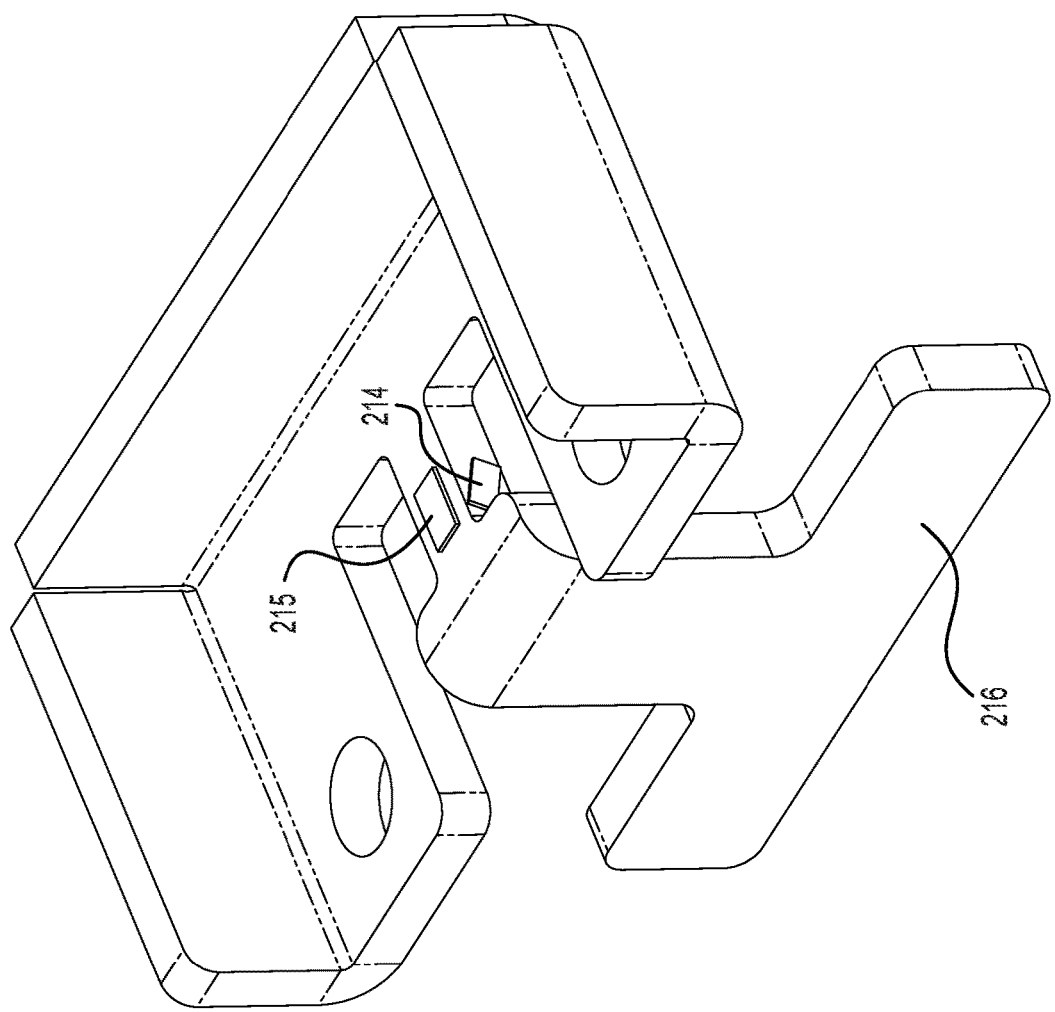

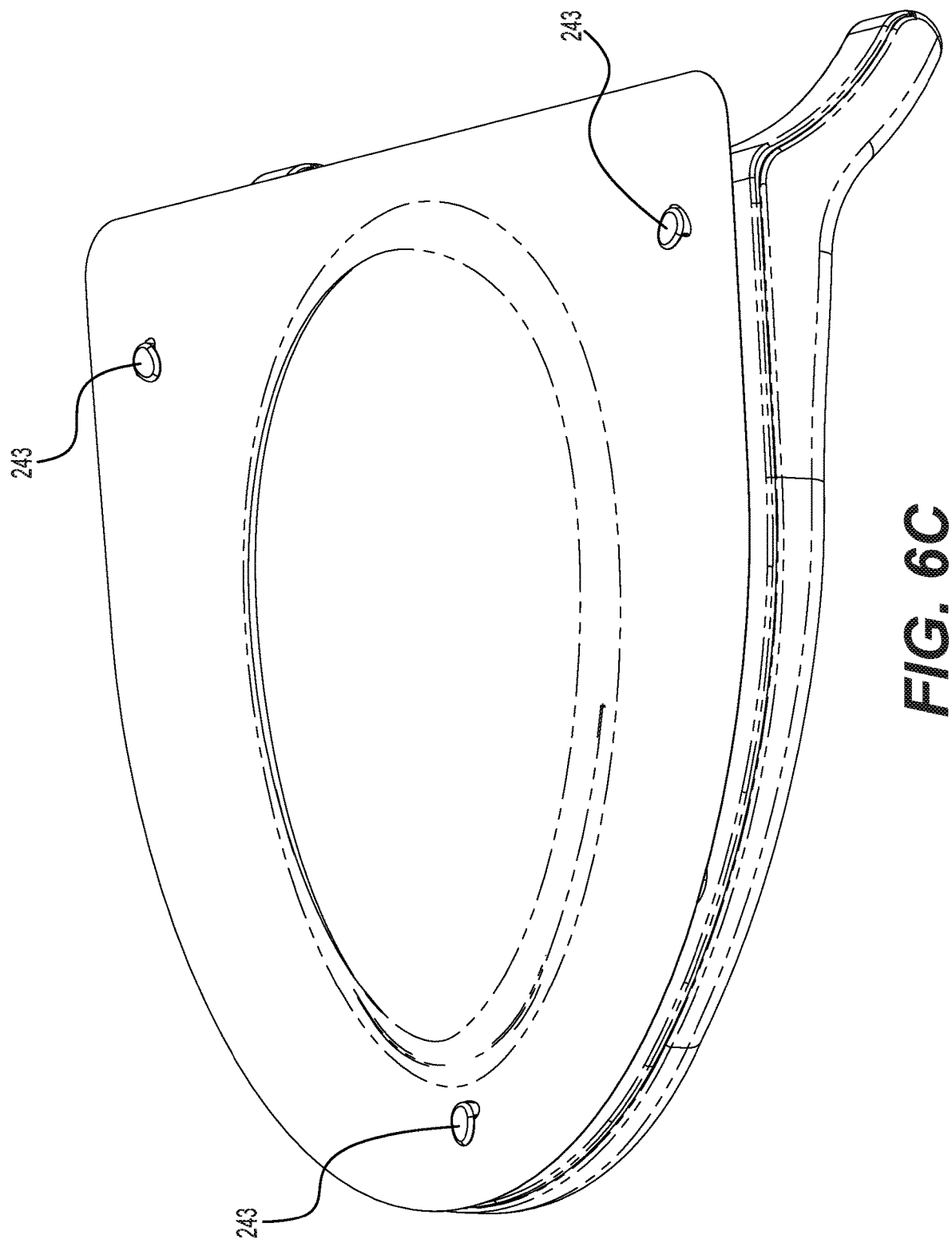

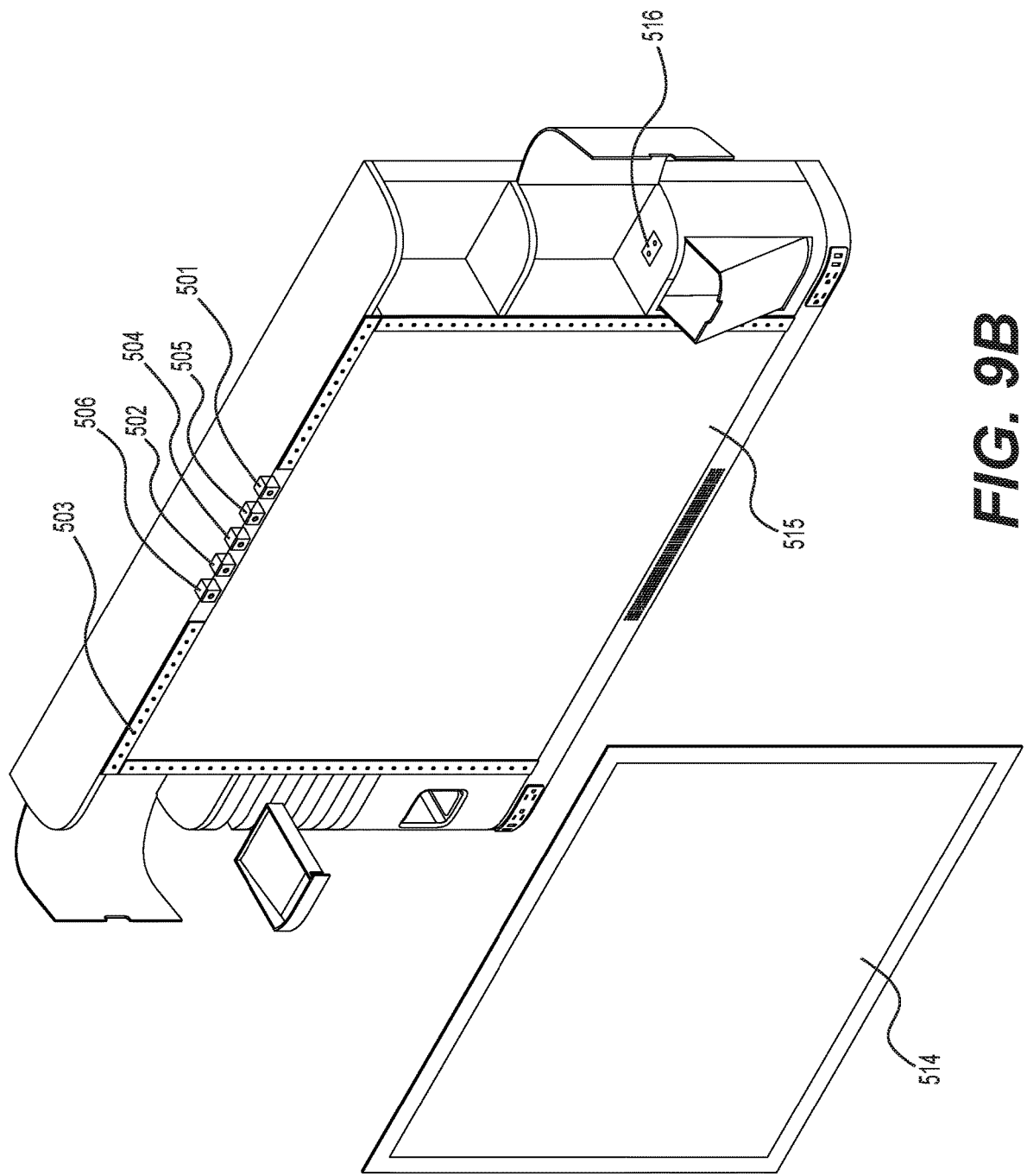

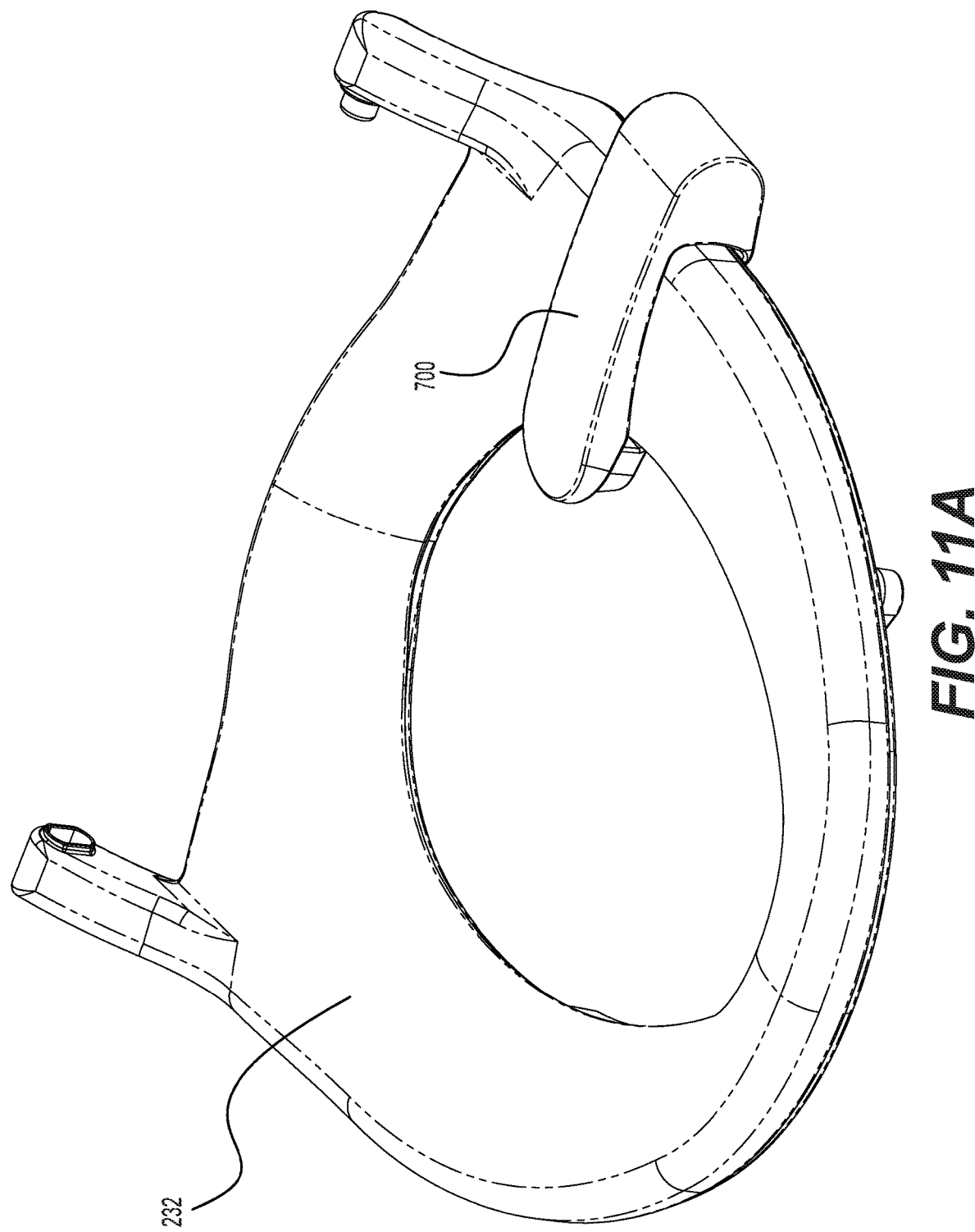

| YES/NO/GRADE | LABEL |
|---|---|
| YES | FORMED STOOL, NO VISIBLE BLOOD |
| YES | UNFORMED STOOL, VISIBLE BLOOD |
| NO | VISIBLE BLOOD |
| YES | DARK URINE |
| NO | DARK URINE |
| YES | CLOUDY URINE |
| NO | CLOUDY URINE |
| 1 | SEPERATE HARD LUMPS OF STOOL |
| 2 | SAUSAGE-SHAPED, LUMPY STOOL |
| 3 | SAUSAGE-SHAPED WITH CRACKS ON THE SURFACE OF STOOL |
| 4 | SMOOTH, SAUSAGE OR SNAKE SHAPED STOOL |
| 5 | SOFT BLOBS WITH CLEAR-CUT EDGE STOOL |
| 6 | MUSHY CONSISTENCY WITH RAGGED EDGE STOOL |
| 7 | ENTIRELY LIQUID STOOL |
| 1 | NO COLOR URINE |
| 2 | PALE STRAW YELLOW URINE |
| 3 | TRANSLUCENT YELLOW URINE |
| 4 | DARK YELLOW URINE |
| 5 | AMBER/HONEY URINE |
| 6 | BROWN URINE |
| 7 | ORANGE URINE |
| 8 | PINKISH URINE |
| 9 | BLUE OR GREEN URINE |

*FIG. 15D*

BIOMONITORING DEVICES, METHODS, AND SYSTEMS FOR USE IN A BATHROOM SETTING

CROSS-REFERENCE TO RELATED APPLICATIONS

This application is a continuation of U.S. patent application Ser. No. 16/016,559, filed Jun. 23, 2018, which is a continuation of PCT/US2018/026618, filed Apr. 6, 2018, which claims the benefit of U.S. Provisional Application No. 62/482,912, filed Apr. 7, 2017, each of which is herein incorporated by reference in its entirety.

BACKGROUND OF THE INVENTION

(1) Field of the Invention

The present application generally relates to biomonitoring. More specifically, the application discloses biomonitoring devices and methods that measure medically relevant excreta and health-related characteristics, and assist in health-related tasks.

(2) Description of the Related Art

It has been recognized that examination of human excreta provides insight into human health. Self-reporting can be performed through diaries, but is subject to interpretation and bias. The ability to objectively and consistently assess excreta on a regular basis can help track symptoms of dysfunction and determine the effects of medications, diet, lifestyle, supplements, and other interventions.

The major components of the American bathroom, including the toilet and mirror, have not fundamentally changed for more than 100 years. In the United States, the toilet mostly lacks any electrical, sensor or network connected capabilities. In Japan, the toilet seat is widely used as an electric bidet for reasons related to hygiene. The vast majority of bathroom mirrors across the world lack any electrical, sensor or network connected capabilities, especially related to health or wellness.

There is thus a need for accurate, convenient and unbiased electronic biomonitoring capabilities that analyze excreta and other health-related characteristics in a bathroom setting. The present invention addresses that need.

BRIEF SUMMARY OF THE INVENTION

The present invention is directed to devices, systems and methods for electronic biomonitoring of characteristics of excreta in a bathroom setting.

Thus, in some embodiments, provided is a biomonitoring device that measures a parameter of a material expelled during use of a toilet by a user. The device comprises a sensor that detects electromagnetic radiation or an analyte chemical in the bowl of the toilet.

Also provided is an embodiment of a biomonitoring device that is a bathroom mirror. The device identifies a user, detects a febrile illness in a user, dispenses medications/supplements, connects to electrical device accessories in the bathroom, and provides an interactive user interface.

Additionally provided is a system for measuring a parameter of a material expelled during use of a toilet by a user. The system comprises the above biomonitoring device.

In other embodiments, a method of determining a physiological parameter of a user is provided. The method comprises expelling a material into the bowl of a toilet in the presence of the above biomonitoring device.

BRIEF DESCRIPTION OF THE SEVERAL VIEWS OF THE DRAWINGS

FIGS. 2A-2F illustrate various views of a seat-integrated toilet device of the present invention. FIG. 2A shows a top perspective view; FIG. 2B shows a bottom view; FIG. 2C shows an exploded view of an image sensor in the device; FIG. 2D shows part of the inside of the device from top perspective cross-section view; FIG. 2E is a close-up view of a load cell in the device; FIG. 2F shows spectroscopic components in the device.

FIG. 3A is a perspective view of the air duct system situated on the bottom of the device; FIG. 3B close-up view of the exit path of air from the air duct system; FIG. 3C is a close-up view of an array of gas sensors in the air duct system.

FIG. 4A is a perspective exploded view and FIG. 4B is a close-up exploded view of the image sensor embodiment.

FIG. 5A is a perspective exploded view; FIG. 5B is a close-up exploded view of the image sensor embodiment.

FIGS. 6A-6C illustrate stool collection embodiments of the present invention. FIG. 6A is a bottom perspective view of an embodiment; FIG. 6B is a cross-sectional view of the embodiment; FIG. 6C is a bottom perspective view of an alternative attachment method of a stool collection embodiment.

FIGS. 9A-9D illustrate a mirror embodiment of the present invention. FIG. 9A illustrates a front perspective view of a wall mounted mirror embodiment; FIG. 9B illustrates a perspective exploded view of a wall mounted mirror embodiment; FIG. 9C illustrates perspective view of the accessories associated with a wall mounted mirror embodiment; FIG. 9D illustrates a touchscreen user interface.

FIG. 10A is a perspective view of the embodiment; FIG. 10B illustrates components of the embodiment; FIG. 10C illustrates the device with wings at 90 degrees; FIG. 10D illustrates the device with wings at 180 degrees; FIG. 10E illustrates the device being opened and awakened from sleep mode; FIG. 10F, FIG. 10G, FIG. 10H and FIG. 10I illustrates representative steps in using the device.

FIGS. 11A-11D illustrate an embodiment of a device of the present invention that clips onto the top of a toilet seat. FIG. 11A illustrates a perspective view of the device clipped onto a seat; FIG. 11B illustrates a cutaway view of the device; FIG. 11C illustrates a cross-sectional view of the device; FIG. 11D illustrates an additional cross-sectional view of the device.

FIG. 12A illustrates a perspective view of the device installed onto a toilet; FIG. 12B illustrates a cutaway view of the device; FIG. 12C illustrates a cross-sectional view of the device.

FIGS. 15A-15D are block diagrams showing exemplary image processing and classification methods for processing data from the devices of the present invention. FIG. 15A shows exemplary image pre-processing tasks; FIG. 15B shows one image classification method for classifying stool consistency; FIG. 15C shows one image classification method for detecting colors in the excreta; FIG. 15D is a set of labels for stool and urine classification.

DETAILED DESCRIPTION OF THE INVENTION

As used herein, the singular forms "a", "an" and "the" are intended to include the plural forms as well, unless the context clearly indicates otherwise. Additionally, the use of "or" is intended to include "and/or", unless the context clearly indicates otherwise.

The present invention is directed to devices, systems and methods for electronic biomonitoring of characteristics of excreta in a bathroom setting.

Thus, in some embodiments, provided is a biomonitoring device that measures a parameter of a material expelled during use of a toilet by a user. The device comprises a sensor or plurality of sensors that detects electromagnetic radiation or an analyte chemical in the bowl of the toilet.

These embodiments are not narrowly limited to any particular biomonitoring device, nor are they limited to the measurement of any particular parameter or any particular expelled material. In various embodiments, the material is feces, urine, flatus, or off-gas from feces or urine.

Figure 1:
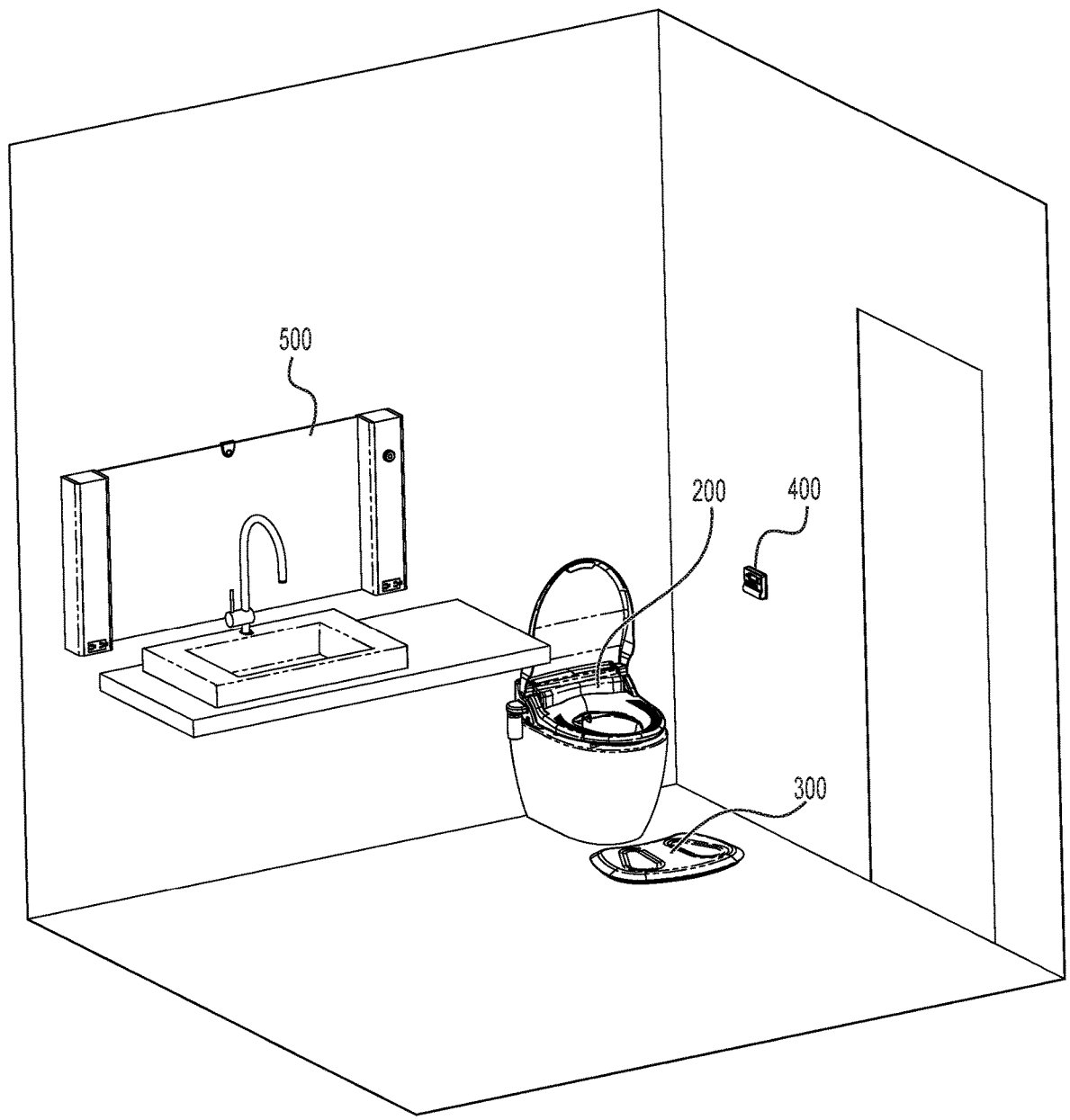
FIG. 1 is a perspective view of a system of the present invention.

FIG. 1 illustrates an exemplary system of the present invention that consists of a toilet 200 where various sensors are integrated into a toilet seat, a foot scale 300, a wall console 400 and a mirror 500 in a bathroom setting. These various components of this system are further discussed below.

Figure 2A:
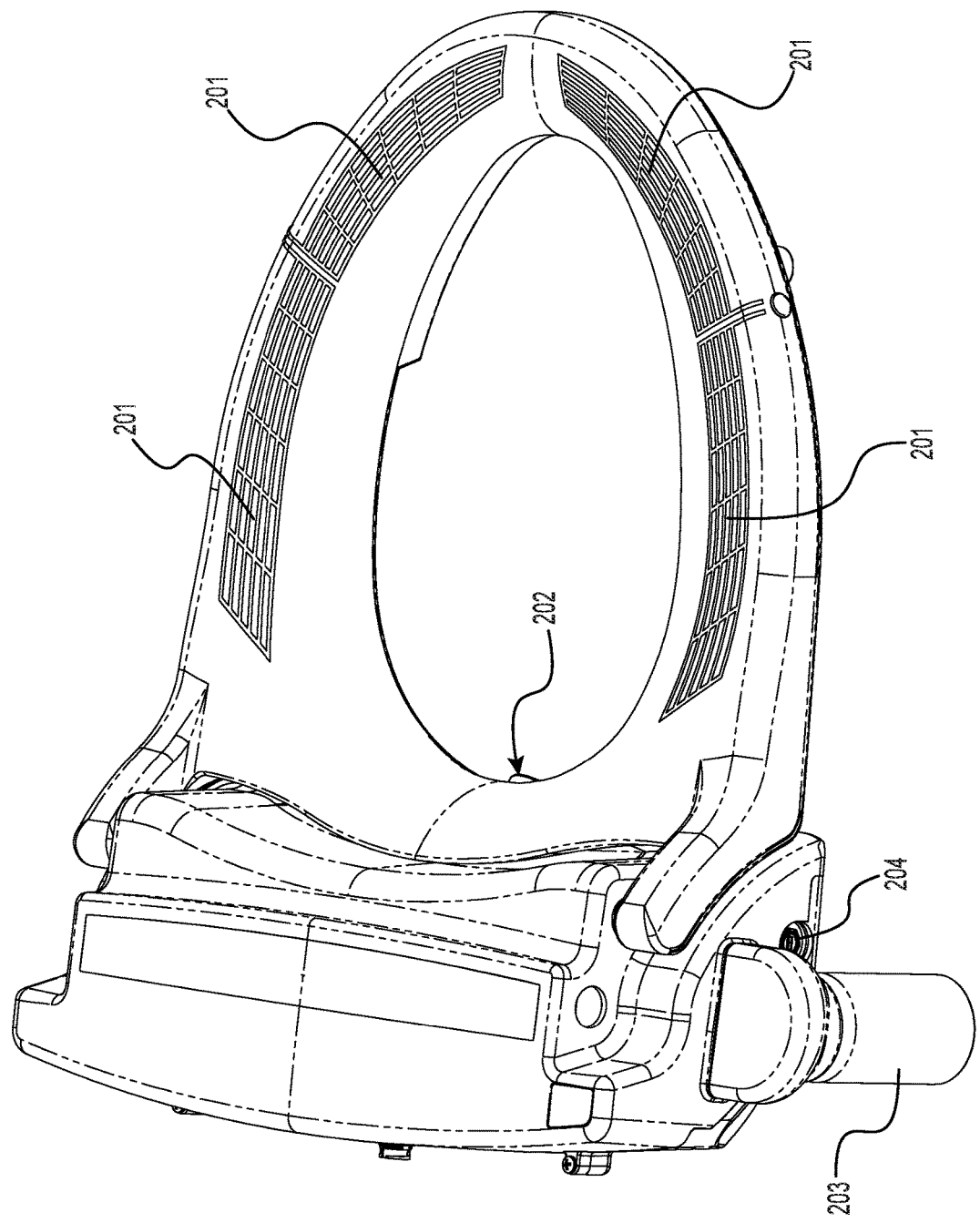

FIG. 2A illustrates the exemplary toilet 200 from FIG. 1. A conductive material 201 is deposited on the apparatus that serves as bioelectrical impedance analysis electrodes. Bioelectrical impedance is determined by applying a sinusoidal current into the body through the electrodes shown in 201. The sinusoidal current is generated with an internal pattern generator and a digital-analog converter. A voltage-to-current converter applies this sinusoidal current into the body, between pairs of two terminals. The voltage created across these two terminals as a result of the impedance of the body is measured back with a differential amplifier, rectified, and its amplitude is extracted and measured by an analog-to-digital converter (ADC). The measured voltage is in direct relation to the body impedance. Common calibration methods and established formulas that can be used to derive the body composition, in some instances, are described in Kushner (1982), Kushner and Schoeller (1986), and Janssen et al. (2000).

The conductive material can be applied to the seat by any method known in the art, or later discovered. In some embodiments, a pad-printable, B-stageable, electrically conductive two-part epoxy adhesive containing carbon filler is applied via tampography on a fixtured device and cured at 100 degrees Celsius for one hour. Sheet resistivity of the epoxy adhesive is between 140-200 ohms/sq/mil. The epoxy adhesive has elongation properties that allow for flexibility e.g., when a user sits on the device, and resists solvents such as common toilet cleaning chemicals and abrasives.

FIG. 2A also shows a nozzle 202 for dispensing liquid, operatively connected to a receptacle 203, that can be replaceable, for containing a liquid, e.g., a deodorizer, chemical reagent, or cleaning agent, to be dispensed into the bowl. A charging port 204 is operatively connected to the battery, which it recharges.

Figure 2B:
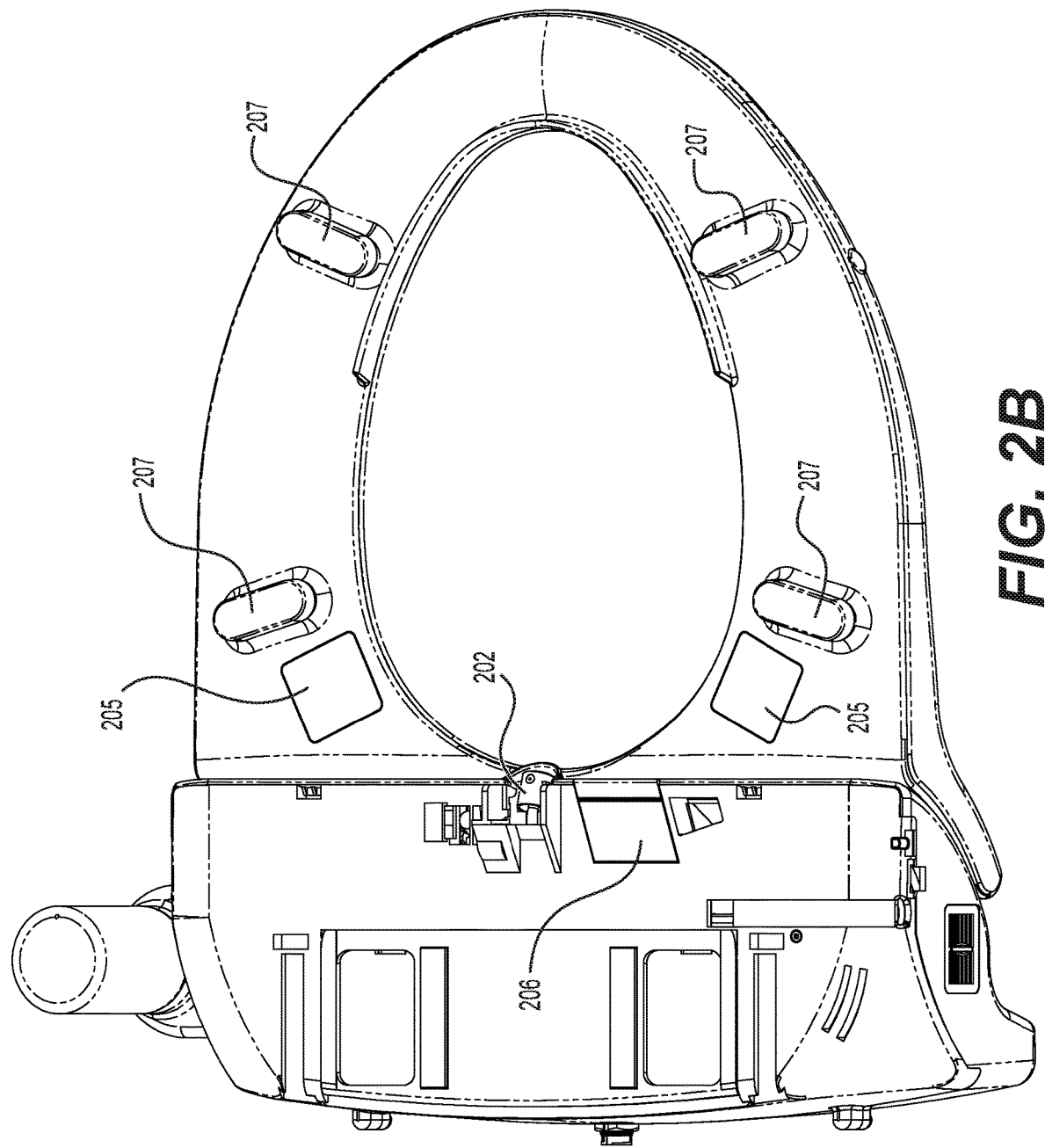

FIG. 2B illustrates the exemplary toilet from a bottom perspective view. Low distortion lenses 205 are provided, which can further comprise hydrophobic and antimicrobial coatings. Electromagnetic radiation can pass through the lenses 205 from the inside of the toilet bowl to an image sensor. An additional or alternative lens 206, similar in material to 205, can be utilized in a position that does not change when the seat is lifted. Behind lenses 205 and 206 are light sources that project electromagnetic radiation in the visible and/or invisible range of the electromagnetic spectrum. Load cells 207 are for capturing the weight of the user. In some embodiments, they pivot to accommodate contact with non-level surfaces, and/or contain anti-skid material where in contact with the toilet bowl.

Figure 2C:
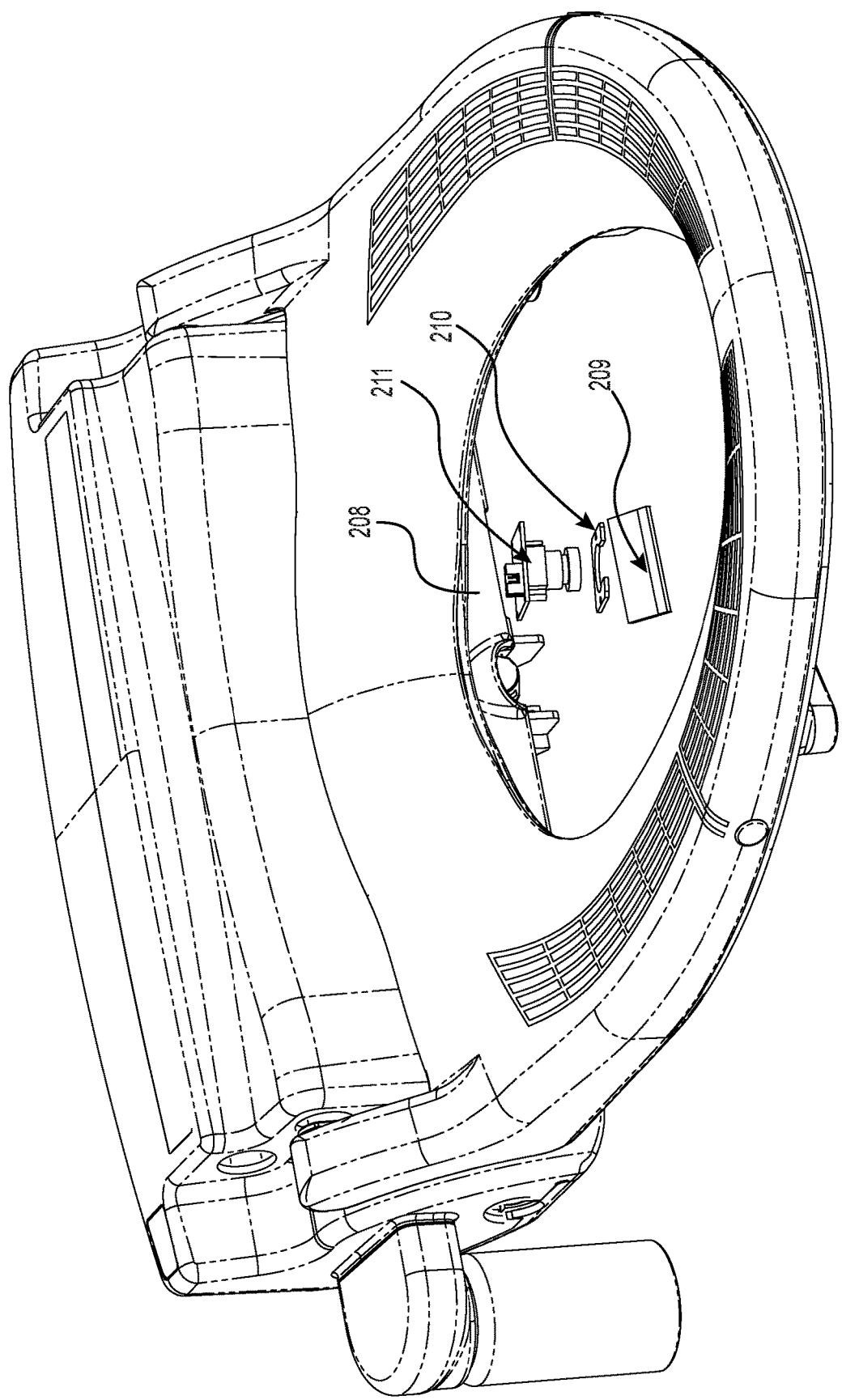

FIG. 2C illustrates an exploded view of the image sensor, light source and lens in an exemplary toilet. The image sensor is in a housing 208. Lens 209, upon which hydrophobic and antimicrobial coatings can be applied, allows passage of electromagnetic radiation of various frequency and wavelengths. An electromagnetic radiation source 210 can emit electromagnetic radiation in the visible and invisible range of the electromagnetic spectrum into a toilet bowl. The visible and/or invisible light captured by the lens can be electronically measured by any means known in the art, for example using an active pixel sensor, for example a charge-coupled device (CCD), or a complementary metal-oxide-semiconductor (CMOS) 211. The light passing through the lens can also be measured using a thermographic array comprised of focal plane arrays that respond to longer wavelengths (mid- and long-wavelength infrared). Illumination of images occurs by turning on the electromagnetic radiation source 210. Capture of images occurs through the sensor 211, which obtains illuminated images inside the toilet bowl at configurable time intervals.

Figure 2D:
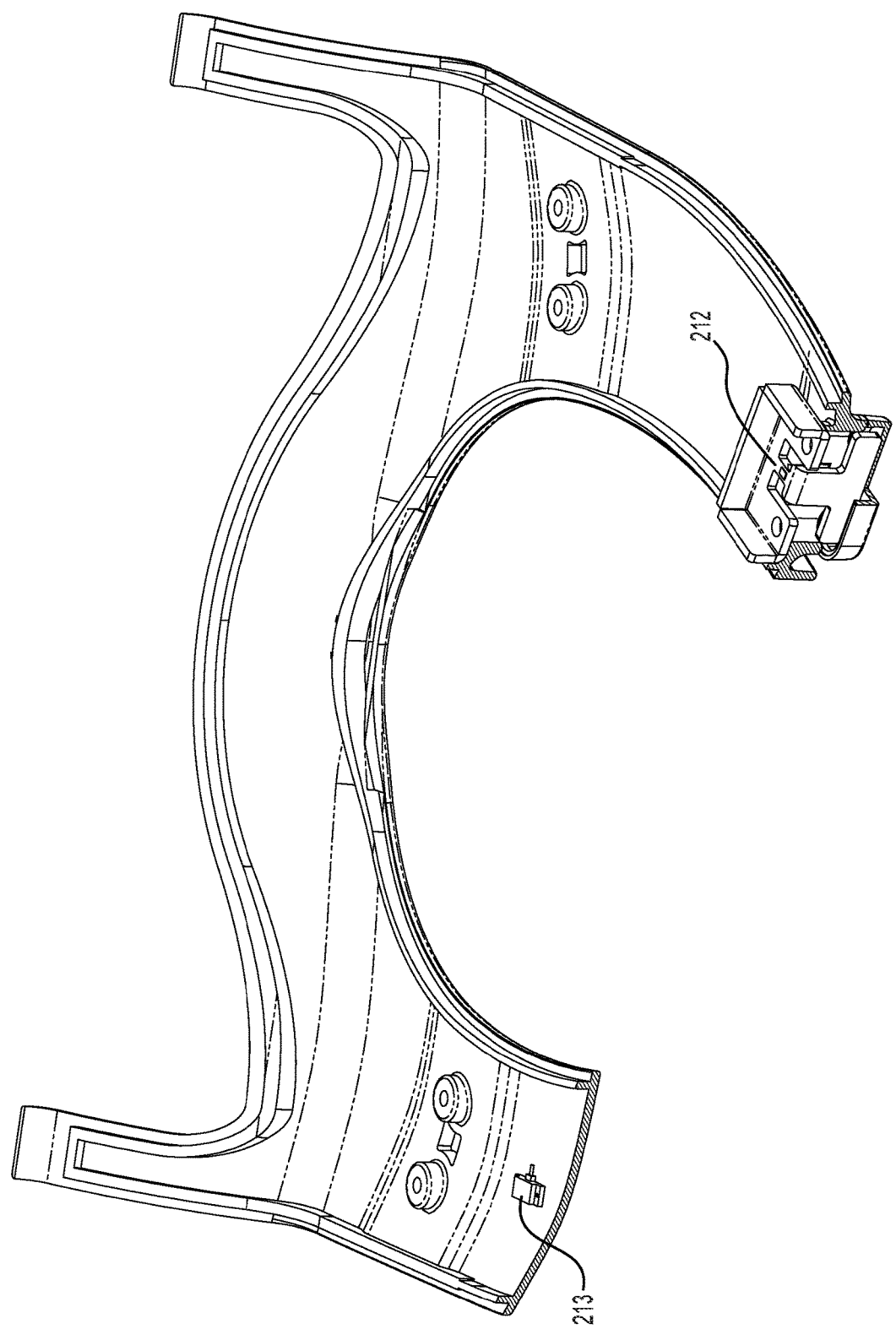

FIG. 2D illustrates part of the inside of the example toilet apparatus from top perspective cross-section view. Load cell 212 captures force in multiple vectors. A load cell that captures force in one vector can also be used, such as a thin film load cell. Capacitive sensor 213 detects user presence while a user is seated on the device. The active presence of a user initiates the sensor measurement and can be used to determine the length of time a user is seated.

FIG. 2E is a close-up view of an exemplary load cell. An additional strain gauge 214 is added to a traditional single-sensor bending-moment force gauge 215. The addition of the strain gauge 214 allows the capture of torque around the sensing beam. This bending moment can be imparted by beam 216 capturing force across the rim of an uneven toilet bowl. The device algorithmically combines torque and bending inputs from the four load cells to calculate the user's weight.

Figure 2F:
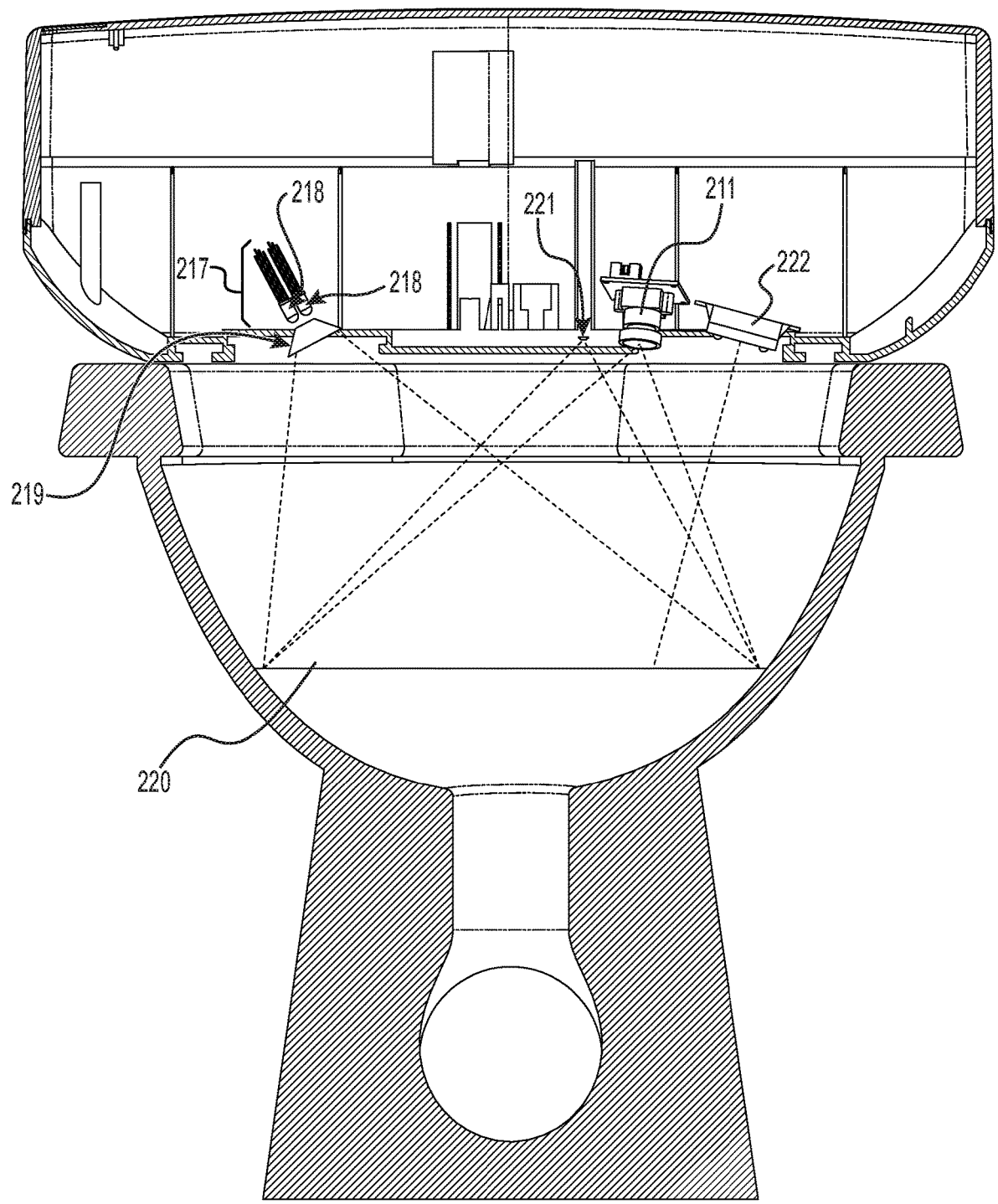

FIG. 2F shows components related to the spectroscopic-based detection of substances such as blood and urine. 217 is a laser diode or photo diode array. 218 is a laser diode, 219 is a prism shape can change position depending on optical requirements, 220 is the top surface of water in the toilet bowl, 211 is an CMOS sensor, 221 is a photosensor or photodetector, 222 is a distance sensor which is intended to reflect off of the top surface of the water in the toilet bowl. Depending on the substance being detected, 218 may emit light at specific wavelengths. The characteristic spectral signature of blood along the near infrared range (760-1500 nm) provides higher selectivity than using solely the visible range (400-780 nm). By utilizing the distance sensor 222 as a power meter, and utilizing Snell's law of reflection by change in index of refraction, the presence and concentration of urine can be measured. 211 may be monochrome with the infrared filter removed. 221 may use single pixel imaging to detect the target substance in the near infrared spectrum. The use of laser diodes compared to a light source such as a light-emitting diodes (LEDs) is the narrower spread in wavelength bandwidth, thus allowing it to be more substance specific. Laser diodes are wavelength specific with full width at half maximum of +−5 nm and require a prism or lens to disperse the laser over the target area (i.e. water table).

The device may also be used with or without added chemicals that manipulate the chemical matter in and on biological cells in the excreta, with which may be useful in detecting the presence of or quantifying blood which may be associated with conditions such as hemorrhoids, ulcerative colitis, colorectal cancer, Crohn's disease, urinary tract infections, and bladder cancer. Such chemicals may be a combination of reagents, buffers, oxidizers or other chemical agents may be liquid or deposited on a substrate that are dispensed into the toilet bowl before defecating or urinating in order to optically display changes in color versus the substrate or provide a photoluminescent glow that can be detected by sensors 211 or 221. An example of such a substrate and color-based blood detection system approved by the US Food and Drug Administration for use with colorectal cancer screening is EZ Detect (Biomerica, Inc., Irvine, Calif., USA).

Figure 3A:
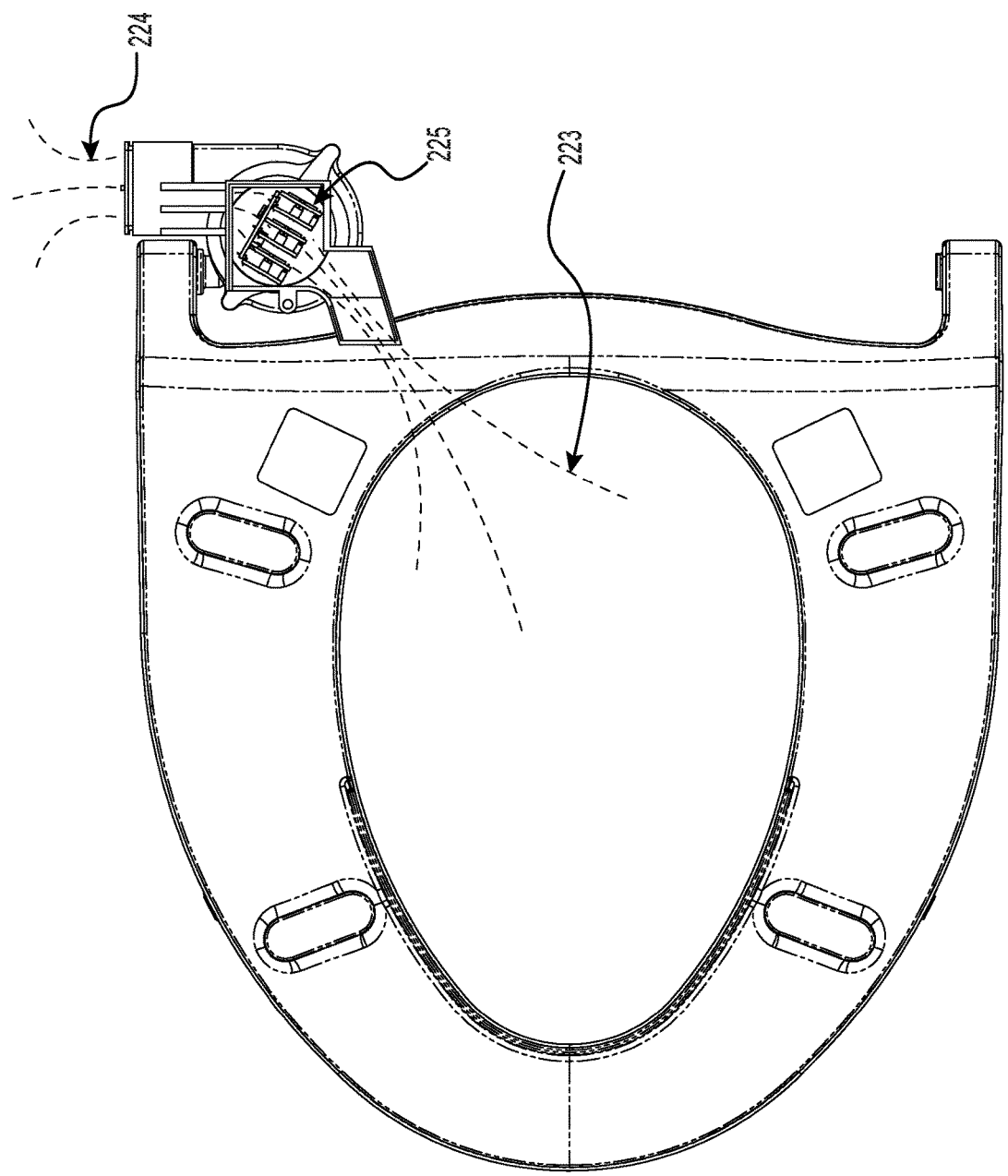
FIGS. 3A-3C illustrate an air duct system in a seat-integrated toilet device of the present invention.

In various embodiments, gaseous chemicals are detected by gas sensors. FIG. 3A illustrates an exemplary air fan and duct that pulls air from inside the toilet bowl through gas sensors. The path of air being pulled from the inside of the toilet bowl 223 and the path of air exiting the toilet seat 224 is shown. A set of gas sensors 225 can be calibrated to detect volatile organic compounds. The mean free path of air going across the gas sensors 225 may be constrained by a wall.

Figure 3B:
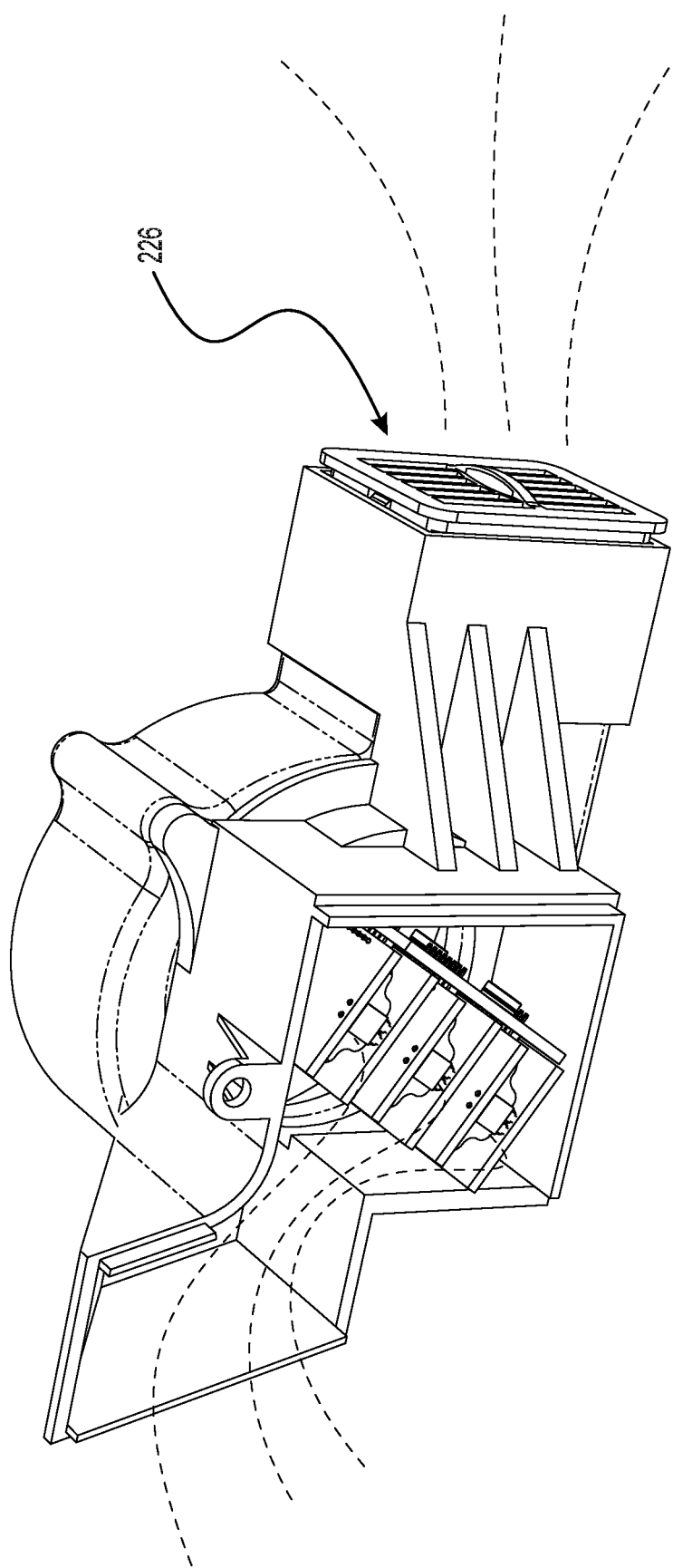

FIG. 3B is a close-up view of the path of air. Filter 226 cleans the air prior to exiting into the bathroom. The filter can be made of any appropriate material, e.g., charcoal.

Any gas sensor known in the art can be utilized as appropriate to detect the gaseous chemicals. In some embodiments, the gas sensor is a micro hotplate metal-oxide sensor.

Figure 3C:
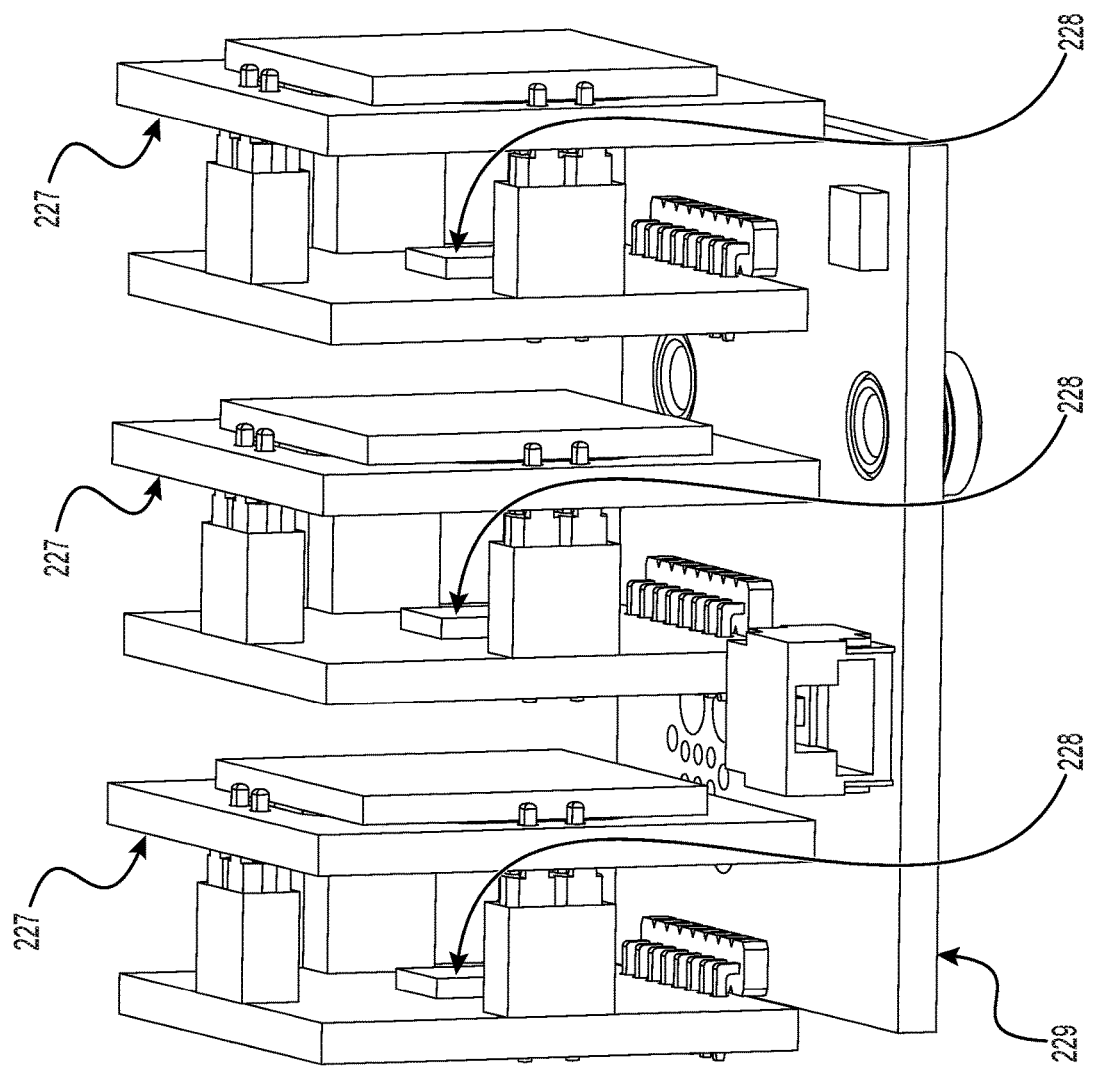

FIG. 3C is a close-up view of exemplary gas sensors. Shown is a combination of three micro hotplate metal-oxide sensors 227, where each blade can have a different spectrum, a transimpedance amplifier 228, and a control circuit board 229, with temperature and humidity sensor and microcontroller. Electrochemical gas sensors may also be used. Some metal-oxides can behave as semiconductors at higher temperatures. Metal-oxide sensors are designed with a heater element and a sensor element (sintered metal-oxide with or without catalyst), separated by a very thin isolating membrane. Redox-reactions occurring at the sensor surface result in changes in resistance, which can be measured. These redox-reactions depend on the nature of the metal-oxide/catalyst, the reacting gas(ses), and the temperature. Depending on sensor type and temperature, a very broad range of substances will give a redox reaction. The gas sensor assembly consists of one or more gas sensors that could be broadband sensors that are responsive to a mixture of gases, as well as narrowband sensors that only respond to concentrations of a particular gas or gases. The actual concentrations can then be computed back using Gaussian mixture models. Because many of the sensors operate with microcurrents and are sensitive to temperature changes, the assembly incorporates a temperature sensor and a chemical sensing front end consisting of a transimpedance amplifier and a cellbias generator. Furthermore, to keep the analog sensing path short, a microcontroller is incorporated in the assembly that converts the readings from the sensors using an ADC to digital signals that can be communicated and processed further through a digital interface as shown.

Any gaseous chemical present in the bowl can be detected in these embodiments. In some of these embodiments, the gaseous chemicals are volatile organic compounds. The volatile organic compounds found in the gut include short-chain fatty acids and branched-chain fatty acids (Gruber et al., 2016). Carbohydrates in the gut are fermented by different bacteria to produce ethanoic, propionic, butanoic, pentanoic, and hexanoic acid acids. Hydrogen sulfide and methanethiol are generated from sulfur-containing substances in the diet. Fermentation of tyrosine and tryptophan leads to the production of phenols and indoles (Zheng et al., 2011). The relative proportions of these different VOCs may reflect the bacterial composition present in the gut.

In some embodiments, the device can be installed with an existing toilet seat (i.e., it does not require replacing the seat). These embodiments are not limited to any particular design, and includes, e.g., a connector that connects a camera or a cellphone to the seat or rim, or any other design. FIGS. 4A, 4B, 5A and 5B provide exemplary embodiments.

Figure 4B:
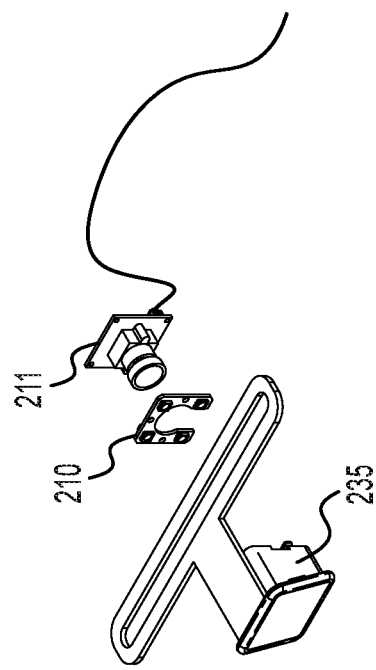
FIGS. 4A and 4B illustrate an image sensor embodiment of the present invention.
Figure 4A:
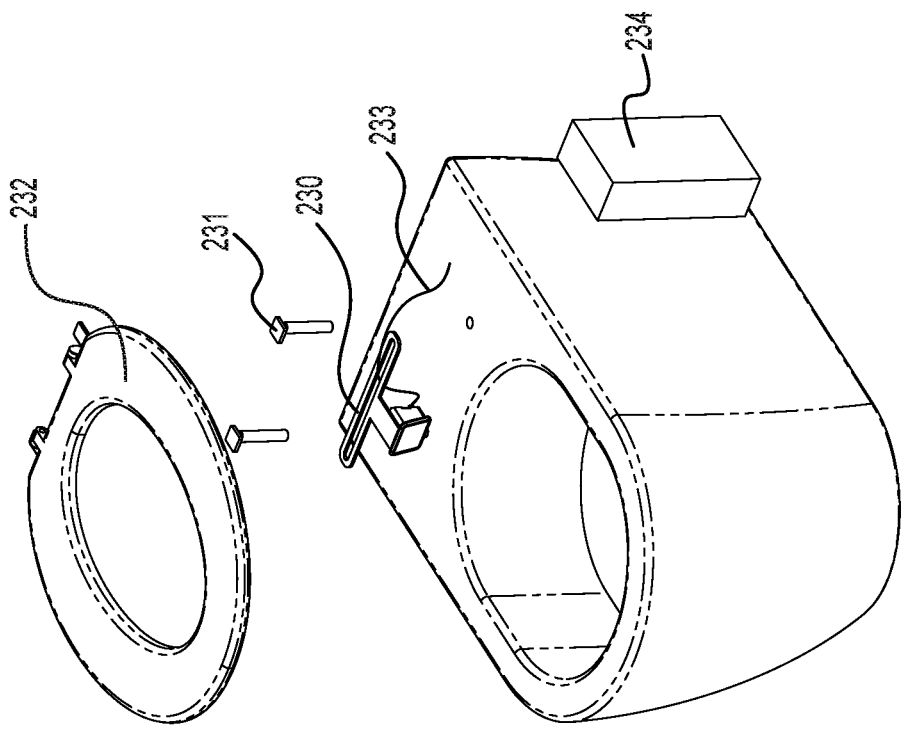

FIGS. 4A and 4B are perspective and close-up exploded views of another embodiment of an image sensor that can work in conjunction with an existing toilet seat (e.g., it does not require replacing the seat). An attachment point 230 is bolted into place with the existing bolts 231 and covered with the existing seat 232. An attachment point that does not require bolting may also be used. A wire 233 is provided that is capable of transmitting power and communications. Power may also be provided through a battery and communications can be wireless. Processing and communications circuitry 234 are also provided, which may or may not be separate from the image sensor. Also shown is housing 235 for the CMOS sensor 211 and an electromagnetic radiation source 210 providing light at various spectra into the toilet bowl. In some embodiments, multiple CMOS sensors may be used. Components related to spectroscopic-based detection of substances may also be used.

Figure 5B:
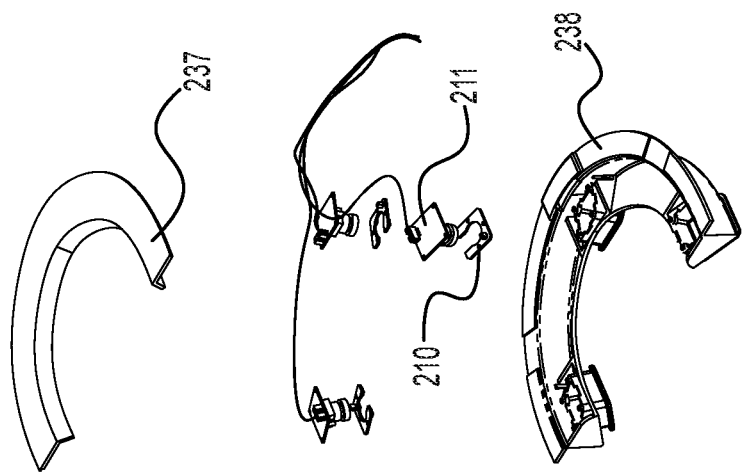
FIGS. 5A and 5B illustrate another image sensor embodiment of the present invention.
Figure 5A:
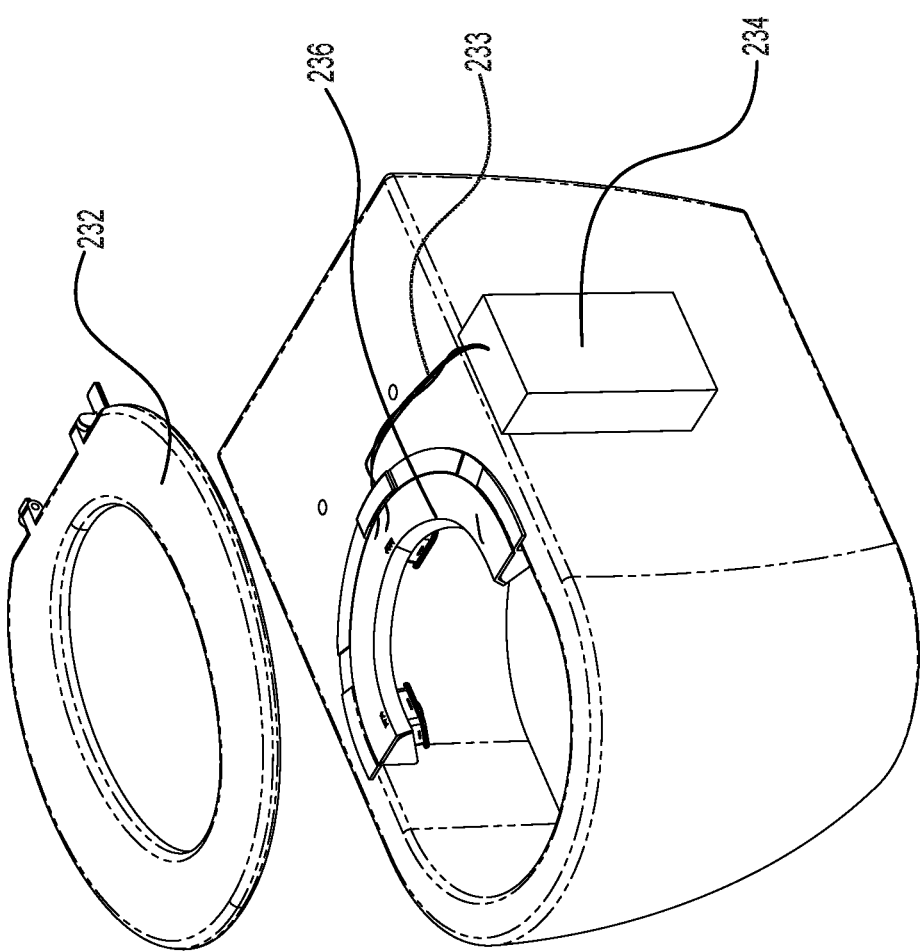

FIGS. 5A and 5B are perspective and close-up exploded views of another embodiment of the image sensor that can work in conjunction with an existing toilet seat. A tray-like apparatus 236 fits into place on top of the toilet bowl rim and is covered with the existing seat 232. A wire 233 capable of transmitting power and communications, and processing and communications circuitry 234 are also included, along with top cover 237. Power may also be provided through a battery and communications can be wireless. An electromagnetic radiation source 210 provides light at various spectra into the toilet bowl, which is captured by CMOS sensor 211. The CMOS sensor is held by apparatus 238. Components related to spectroscopic-based detection of substances, e.g., as described above, may also be used. This device may be partially or completely sealed.

Figure 6A:
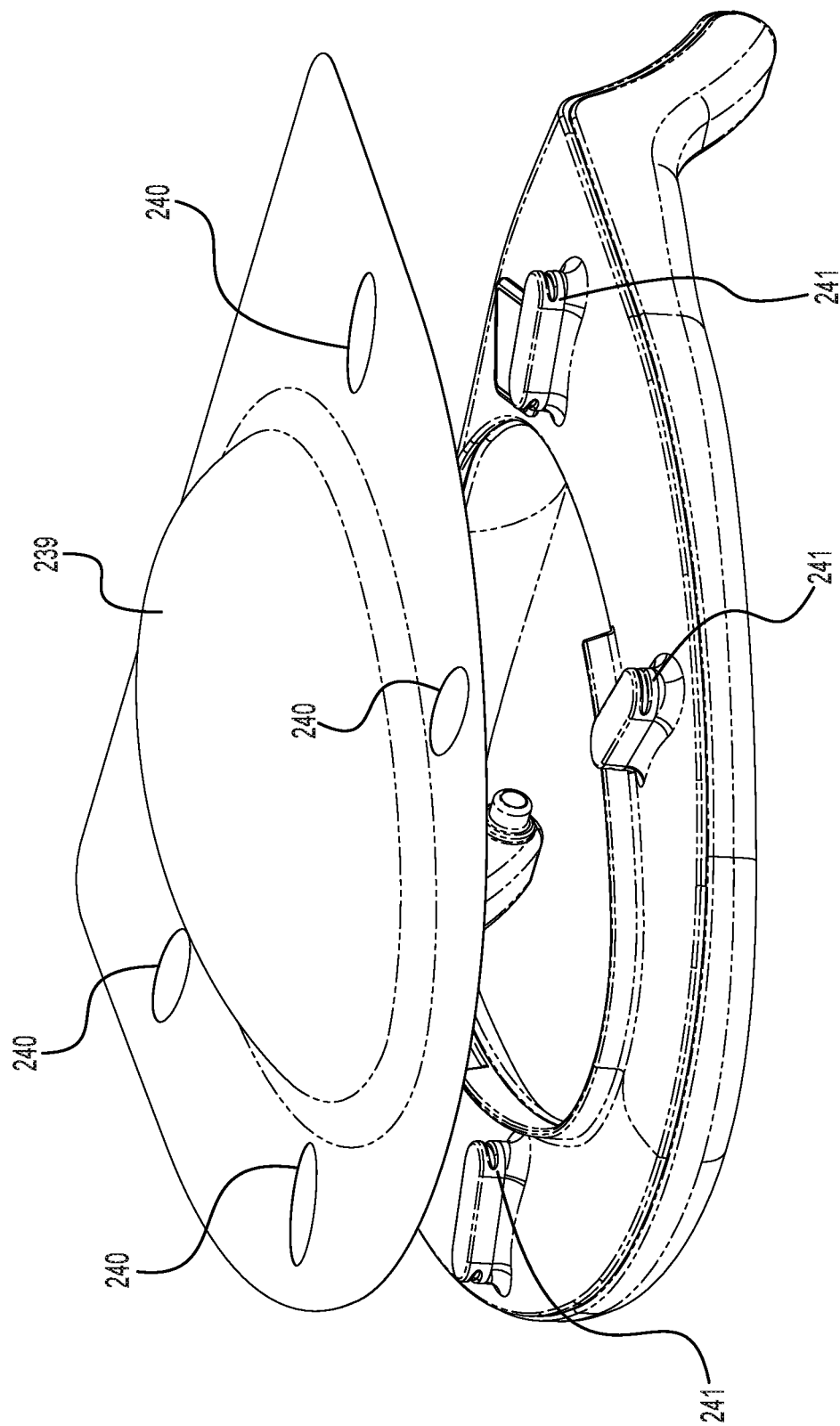
Figure 6B:
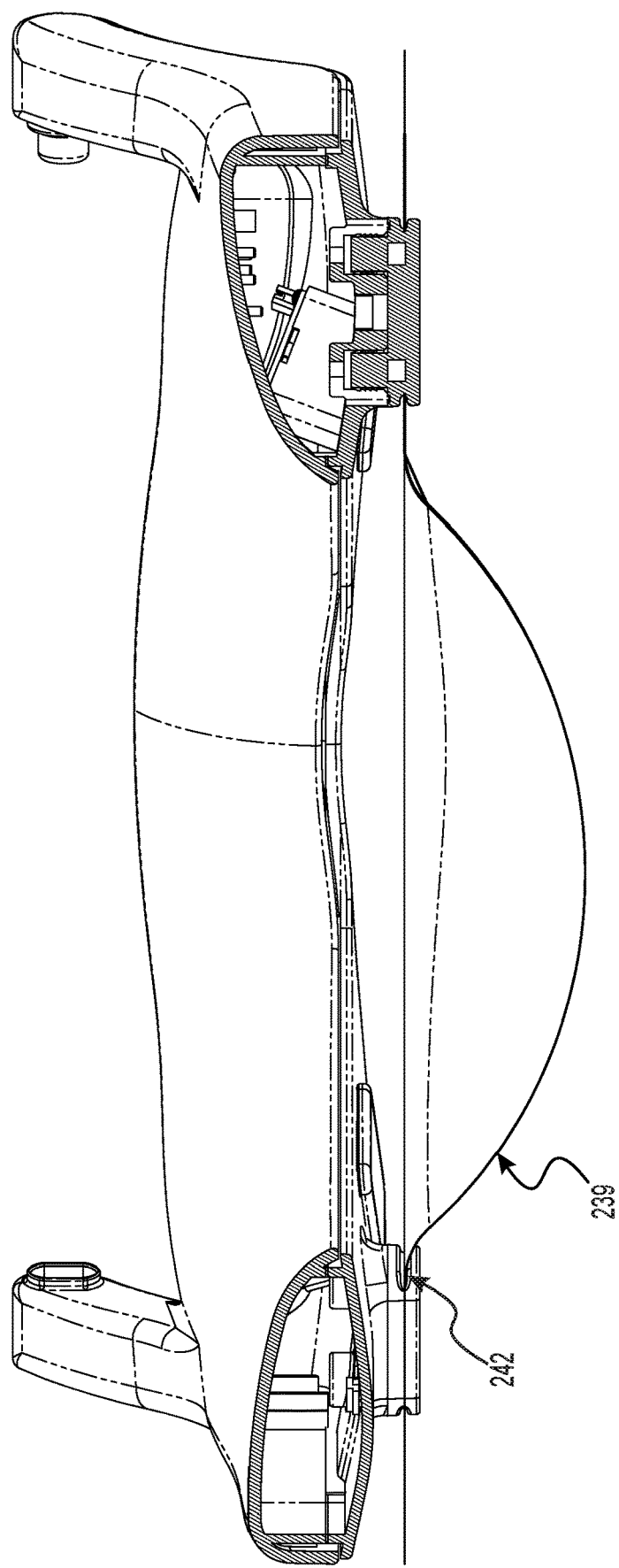

A flushable stool collection system is also provided. FIGS. 6A and 6B are bottom and cross-section views of such an exemplary system with a toilet seat. Stool collector 239 is constructed with a water-soluble material such as polyvinyl alcohol. Holes 240 in the stool collector attach the stool collector to the toilet seat in conjunction with modified feet on the toilet seat 241, where the hoes hook over the modified feet. Another view of the feet 242 depicts an exemplary location where the stool collector 239 can be fastened.

An alternative embodiment of fasteners 243 in a stool collection system is shown in FIG. 6C. Those fasteners can be used as an alternative to the fasteners at the toilet seat feet shown in FIGS. 6A and 6B.

In additional embodiments, the system further comprises a foot scale designed to be placed on the floor that performs any or all of the following functions: calculate, measure, assess and/or determine physiologic data.

Figure 7:
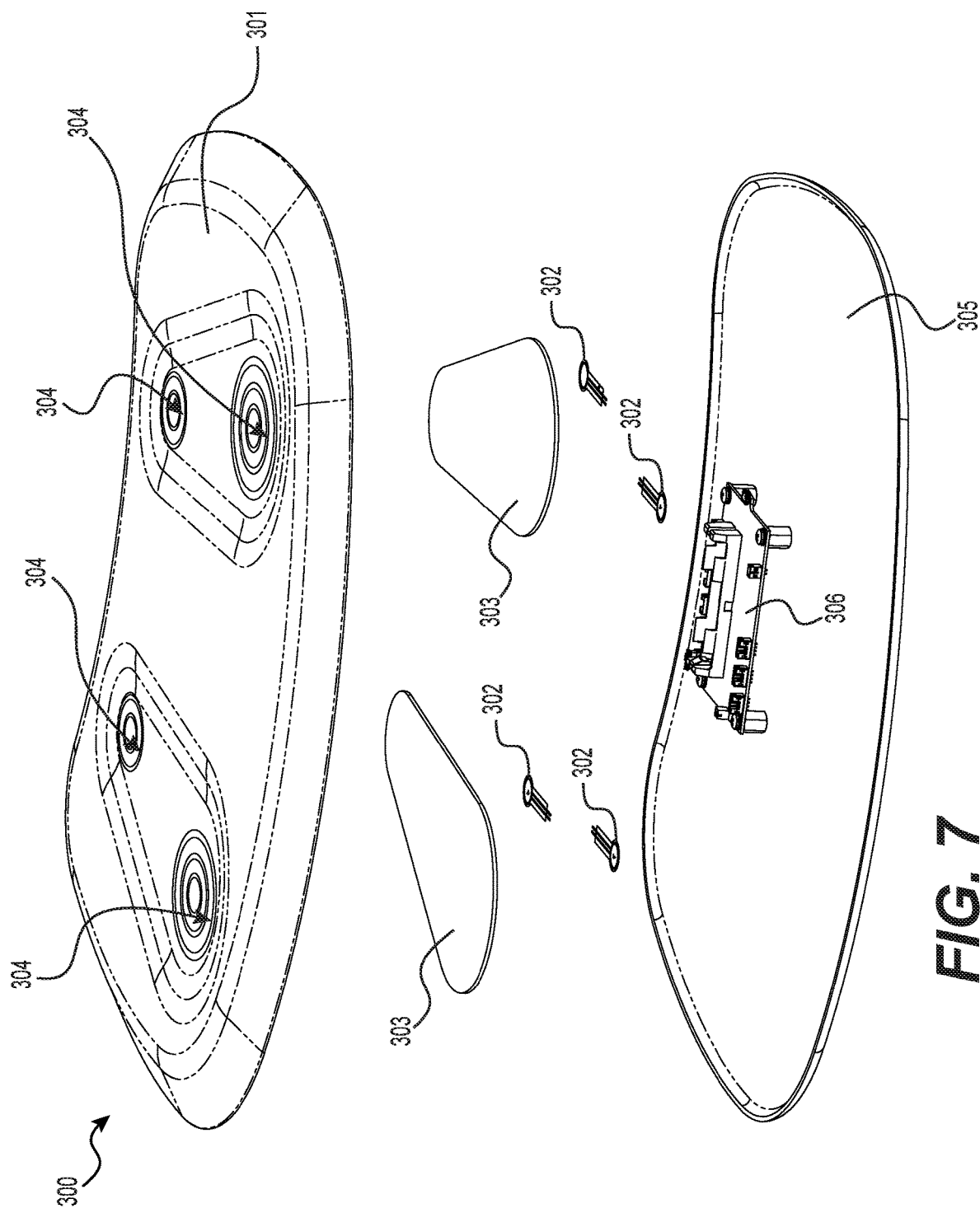
FIG. 7 is an exploded view of a foot scale embodiment of the present invention.

FIG. 7 is an exploded view of exemplary scale or footstool 300. Mat 301 is close to the ground and has sloping edges that can prevent users from injuring themselves when using the device and also contains guides where users can place their feet. Thin film pressure sensors 302 can capture the weight placed on the guided area indicated in 301 and transmitted through 303. In other embodiments, 302 is a load cell. Conductive material 304 serves as bioelectrical impedance electrodes, measuring bioelectrical impedance through the feet. Base 305 can rest on the floor of a bathroom. Processing and communications circuitry 306 includes a battery holder.

In further embodiments, the system comprises an electronic console that performs any or all of the following functions: measure ambient light, determine user presence, identify user, and/or has a user interface to display physiologic information. In various embodiments, the displayed physiologic information is any or all of the following: current information, historical information and/or current information in view of historical information.

Figure 8:
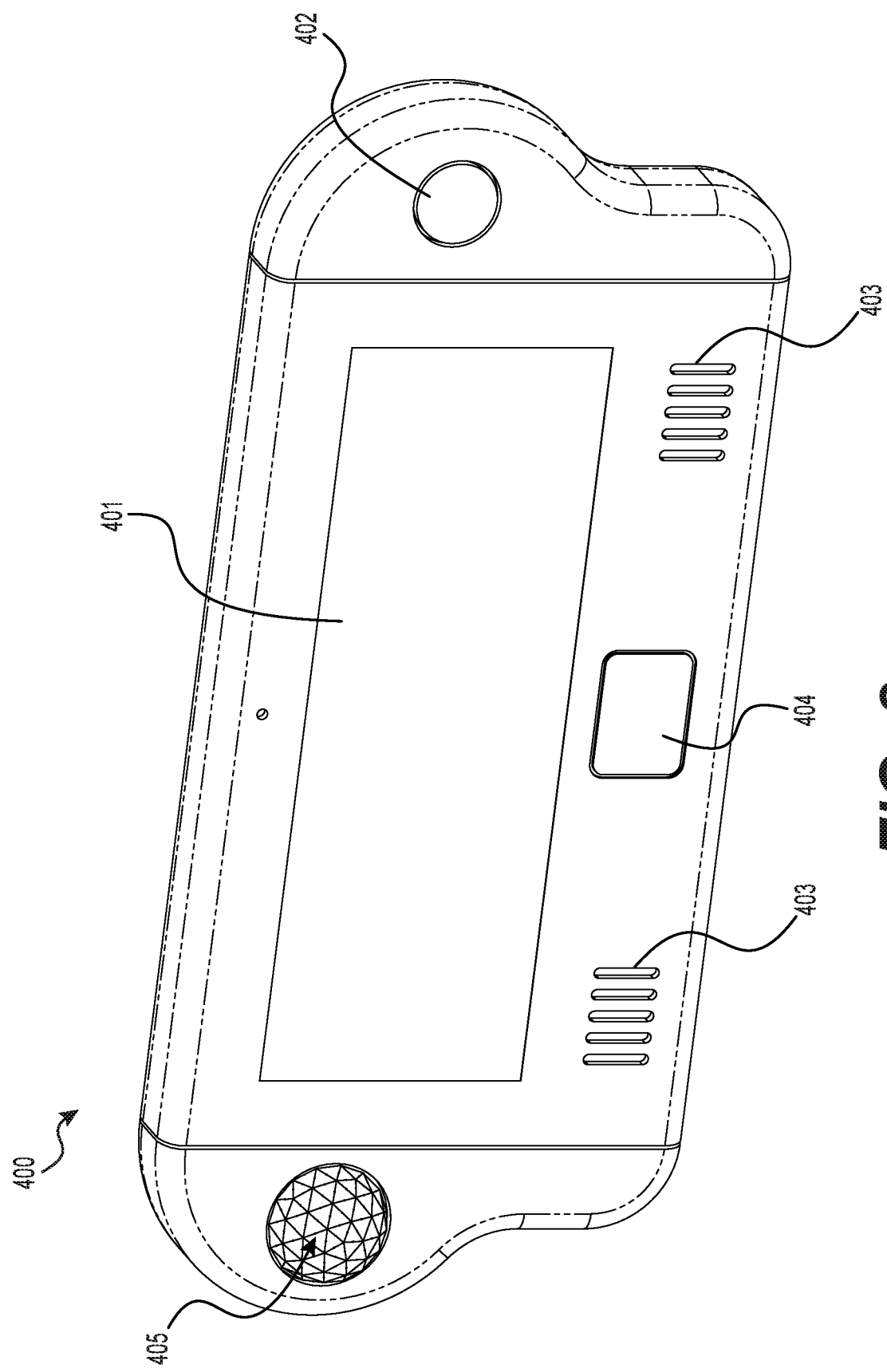
FIG. 8 is a perspective view of a wall console of the present invention.

FIG. 8 is a perspective view of an exemplary console system 400. Electronic display 401 provides real-time information to the user as he sits on the toilet, such as weight and body composition. Ambient light detection sensor 402 is also included in these embodiments. Speakers 403 are also present, through which audio feedback can be provided, e.g., indicating to the user that he has been successfully identified. Fingerprint sensor 404 is an example of an identification method that uniquely identifies the user. Passive infrared sensor 405 can be used to detect user presence.

Any of the above-described devices may also comprise any other bathroom-related component including but not limited to: an electric or non-electric bidet; a presence-activated night light; ambient lighting of different colors; a heated toilet seat; a foot warmer; a voice- or gesture-activated toilet flush; a toilet cover that opens/closes automatically; and a networked speaker to play music.

Also provided is a bathroom mirror device, which may be non-portable or portable in nature, that performs any or all of the following functions: identify a user through facial recognition; detect a febrile illness in a user; dispense oral medications and supplements; gather data from portable electronic device accessories that may include a core temperature thermometer, toothbrush, shaver, breath sensor, otoscope, opthalmoscope, stethoscope, pulse oximeter, and blood pressure monitor; and provide an interactive user interface.

Figure 9A:
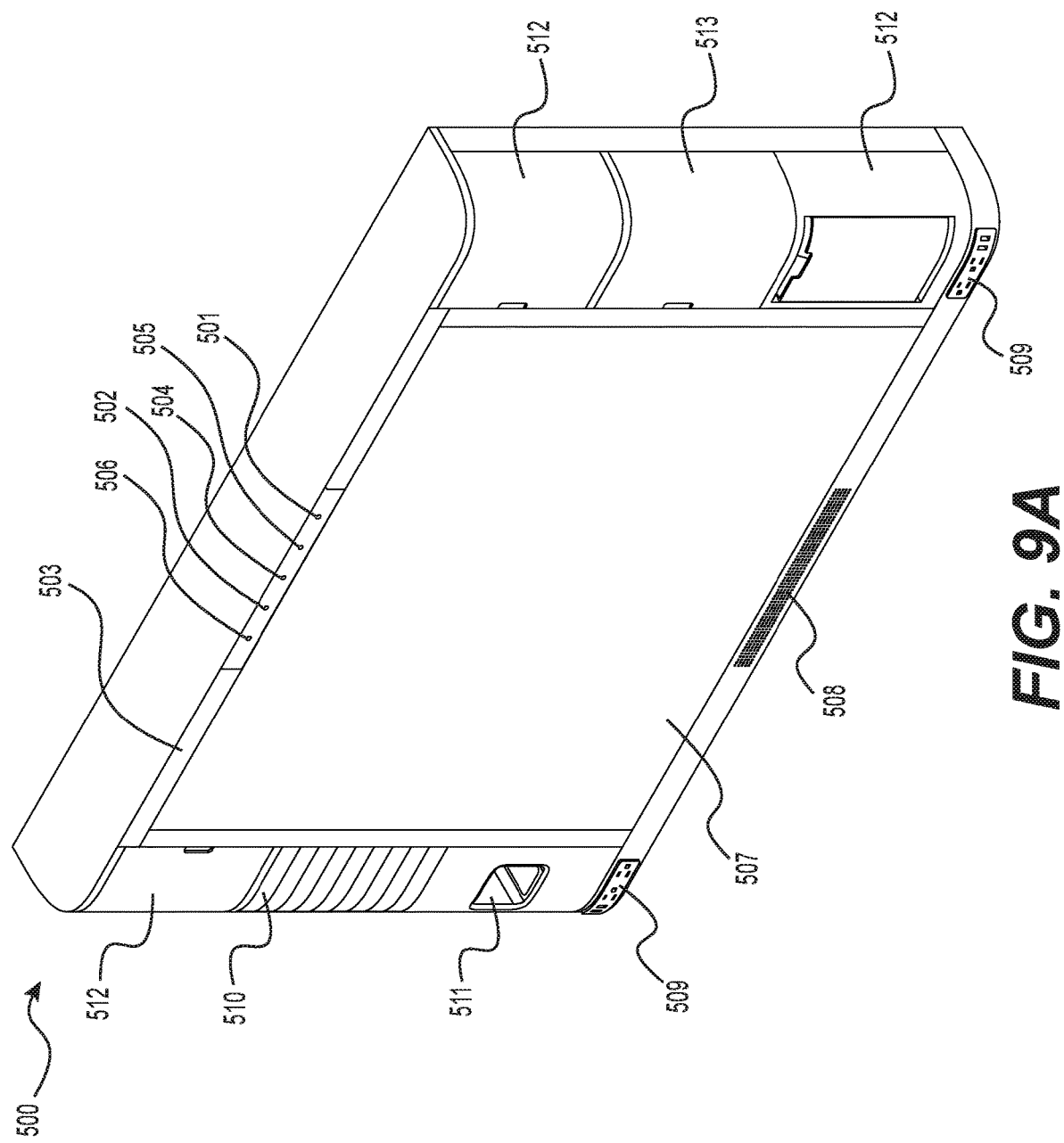
Figure 14:
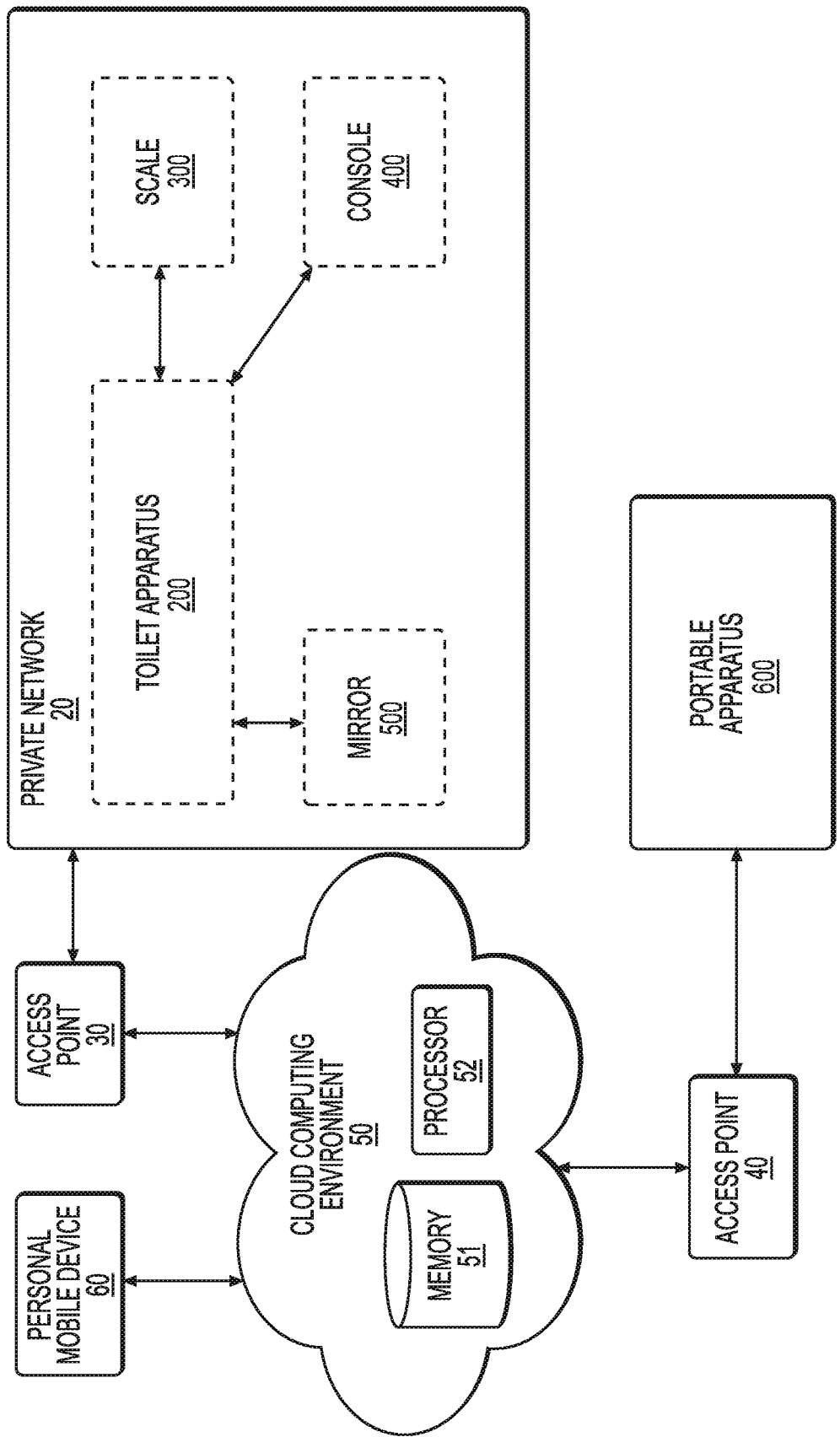
FIG. 14 is a block diagram that shows an exemplary communications network architecture, devices, and components for operating the devices of the present invention.

FIG. 9A illustrates a front view of an exemplary wall-mounted mirror 500 powered by mains electricity and connected to a private network 20 (FIG. 14). Ambient light sensor 501 detects ambient light conditions. Passive infrared sensor 502 detects user presence. LED lighting 503 illuminates the face and body of a user. An array of laser diodes 504 in combination with image sensor 505 is used to identify a user in a bathroom setting based on facial recognition techniques. A thermal sensor 506 is used to detect elevated temperature in a febrile user. Screen 507 serves as both a mirror and a touch display. Microphone and speakers 508 provide audio input through which a user's voice can be captured and audio output, such as from an artificially intelligent agent, that can interact with the user. Power outlets 509 such as universal serial bus and alternating current sockets are present. Pill pack cartridge 510 contains medications and/or supplements. Pills are combined and dispensed in pre-determined dosages through pill dispenser 511. Storage 512 is provided, as well as a charging dock 513 for accessories.

FIG. 9B shows an exploded perspective view of the components of mirror 500. A touchscreen display 514 is placed over a one-way or transparent mirror 515. A charger 516 for accessories that connect to 500 may be inductive or wireless in nature. The charging embodiments described herein are not narrowly limited to any particular mechanism or device used for charging.

Figure 9C:
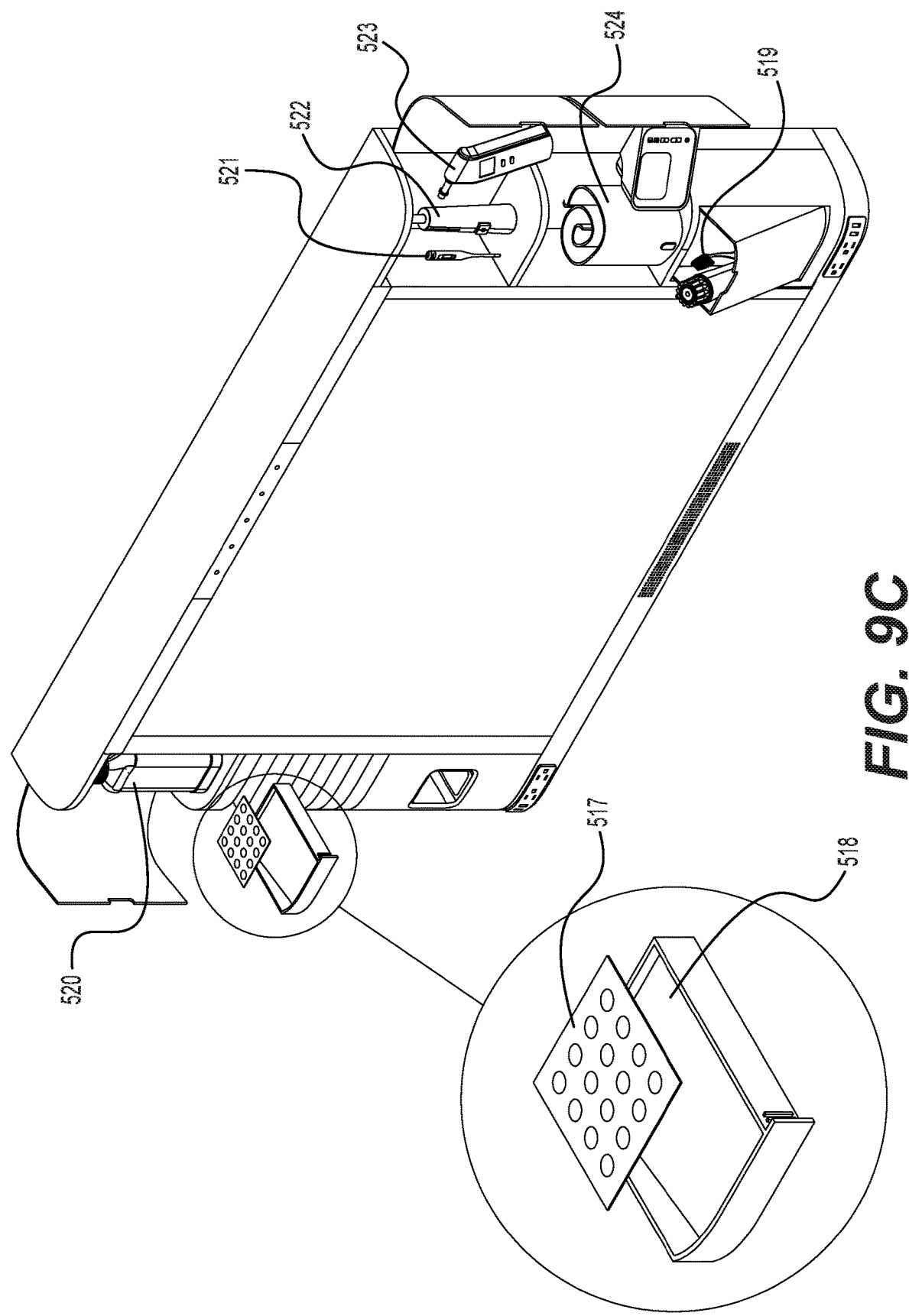

FIG. 9C shows a more detailed view of the pill dispensing system and exemplary accessories. Pills of a particular medication or supplement are sealed in a pack 517 and placed in cartridge 518. Pills may be combined in a way that facilitates dispensing the correct dosages. Toothpaste 519 and mouthwash 520 are stored in storage 512. Exemplary electrical devices shown that connect to the system include a thermometer 521, toothbrush 522, breath sensor 523, and blood pressure monitor 524.

Figure 9D:
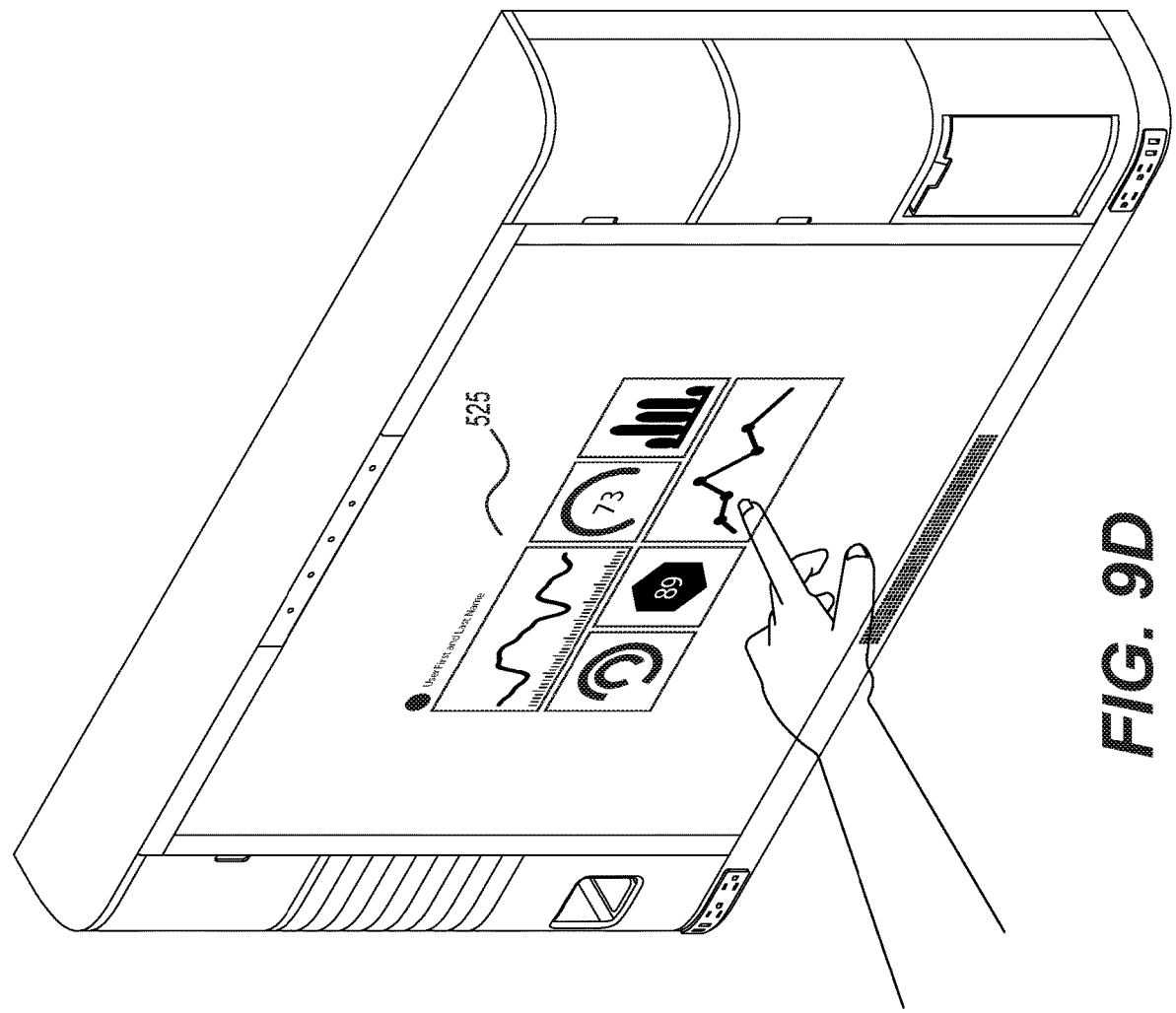

FIG. 9D shows an interactive user interface 525 in which the user may use a touchscreen to interact with current and/or historical information that is gathered from toilet apparatus 200, scale 300, console 400, mirror 500, electrical device accessories that connect to system, the user themselves, or through any type of data source which can be connected to the system. The user may also interact with the system through voice. The interface may perform, but is not limited to, the following functions: obtaining information from the user; providing current/historical information to the user; alerting the user; dispensing medications/supplements to the correct user; determining user compliance in taking medications/supplements; facilitating the dispensing of medications/supplements at the recommended time; changing dosing of medications/supplements; sharing information about the user to others; and facilitating the provision of telemedicine through remote consultations and information gathered by the system.

Figure 10A:
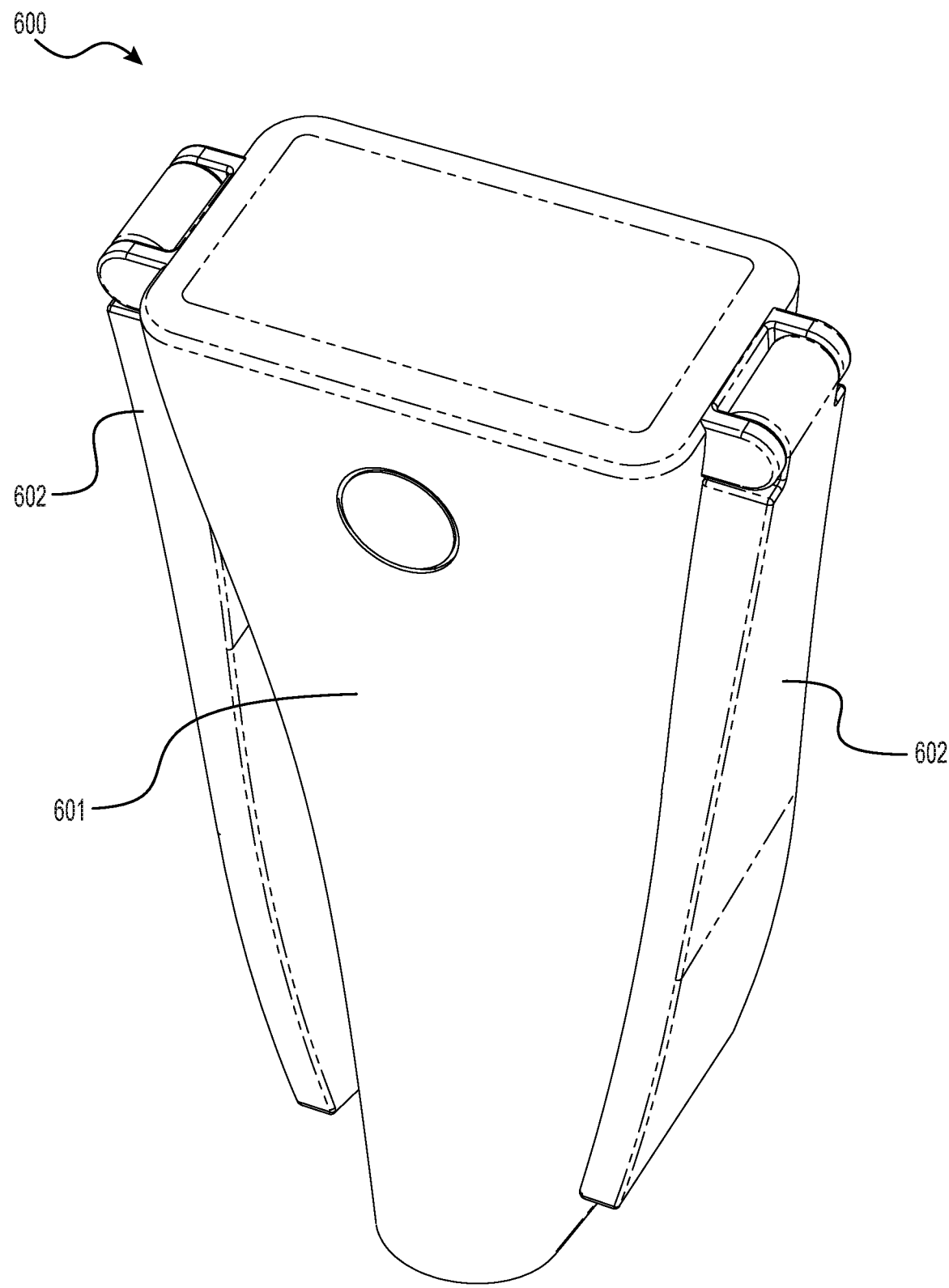
FIGS. 10A-10I illustrate a portable embodiment of a device of the present invention.

FIG. 10A shows a representative portable device 600 comprised of body 601, sealed from liquid ingress and smooth with minimal crevices for easy cleanability, made out of a polymer with antimicrobial properties; with movable wings 602 comprised of a textured elastomeric material that allows for secure grip.

Figure 10B:
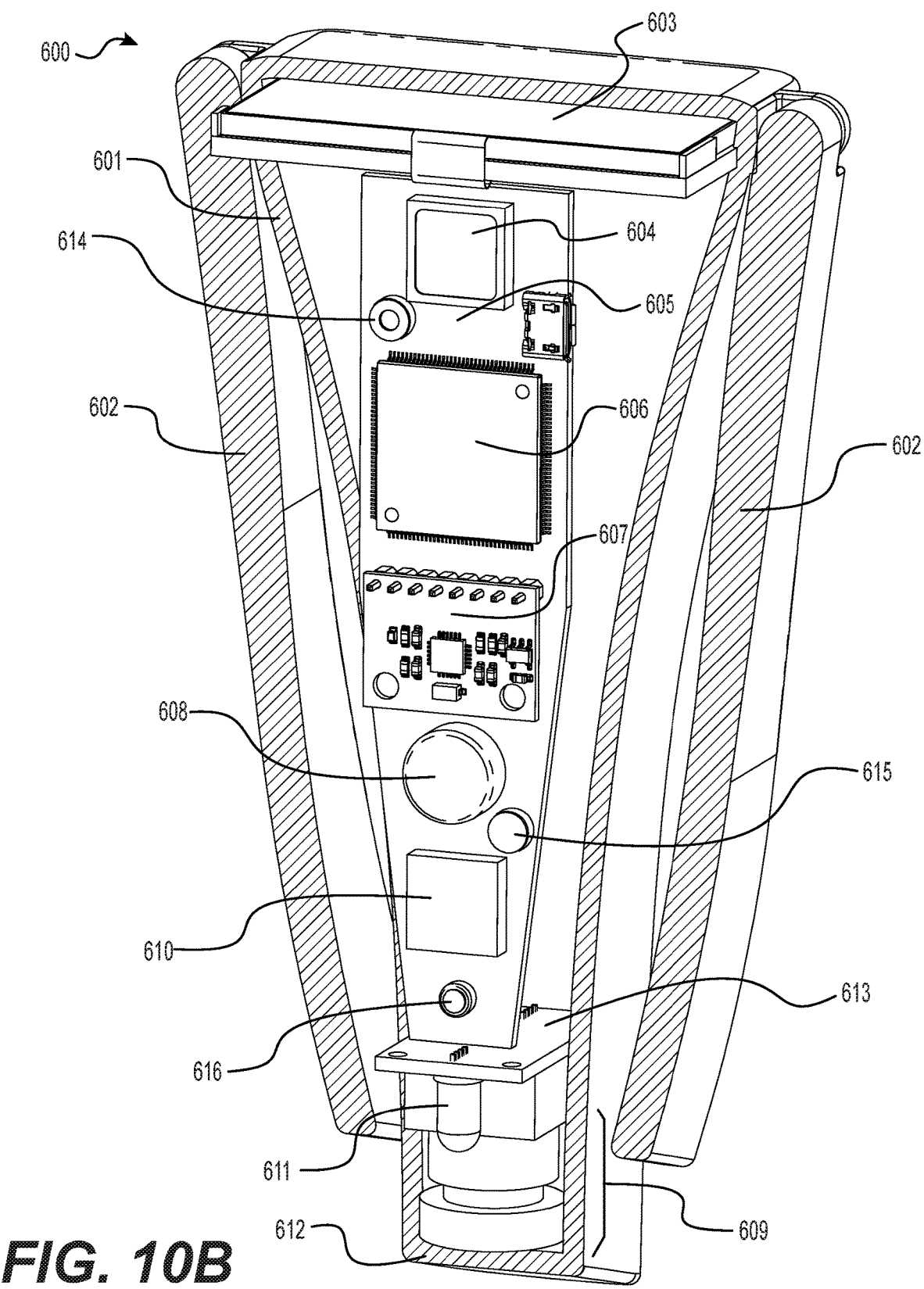

FIG. 10B shows the components of 600, with wings 602 in the down position, where the device is ready to be transported. The top area consists of a capacitive touchscreen panel 603. The middle area includes fingerprint sensor 604 where the user is meant to place his or her finger on to be identified, printed circuit board assembly 605, module chip 606 containing logic and communications hardware and components, three-axis accelerometer 607, battery 608, image sensor assembly 609, and data storage unit 610. On the bottom, there is an electromagnetic radiation source 611 capable of emitting electromagnetic radiation in the visible and invisible range of the electromagnetic spectrum into the toilet bowl, a lens 612 of low distortion upon which hydrophobic and antimicrobial coatings can be applied, and a CMOS sensor 613. The CMOS sensor 613 may also be a thermographic array comprised of focal plane arrays that respond to longer wavelengths (mid- and long-wavelength infrared). Components for spectroscopic detection and analysis, e.g., as described above, can also be included.

In some embodiments, placing the wings 602 of the device in this down position turns the device off, e.g., when the user finishes the bowel movement and/or urination and wishes to put the device away in order to free his or her hands. A speaker 614 allows sounds to be played and haptic feedback is provided through 615. A microphone 616 allows the user's voice to be captured.

Figure 10C:
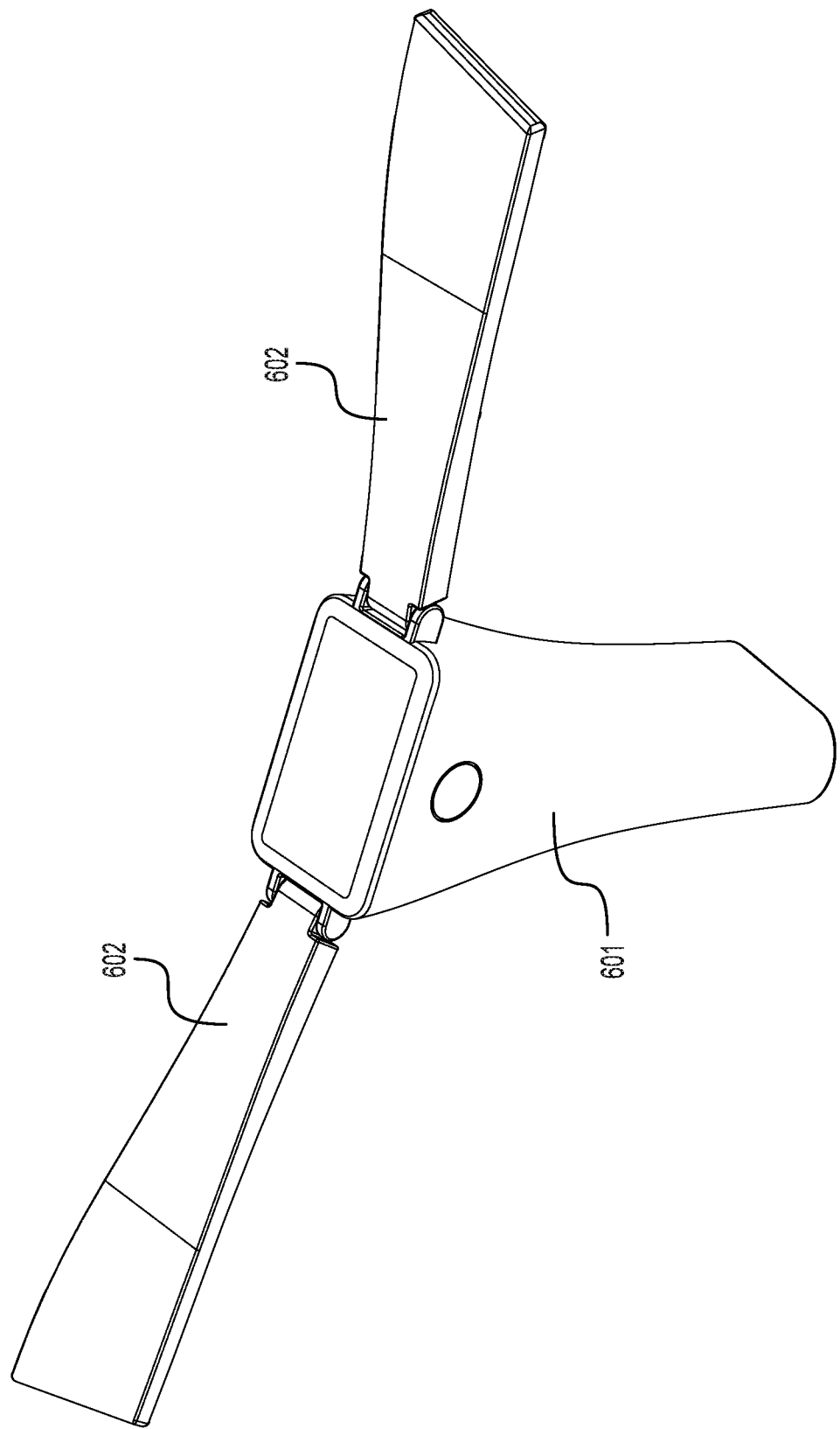
Figure 10D:
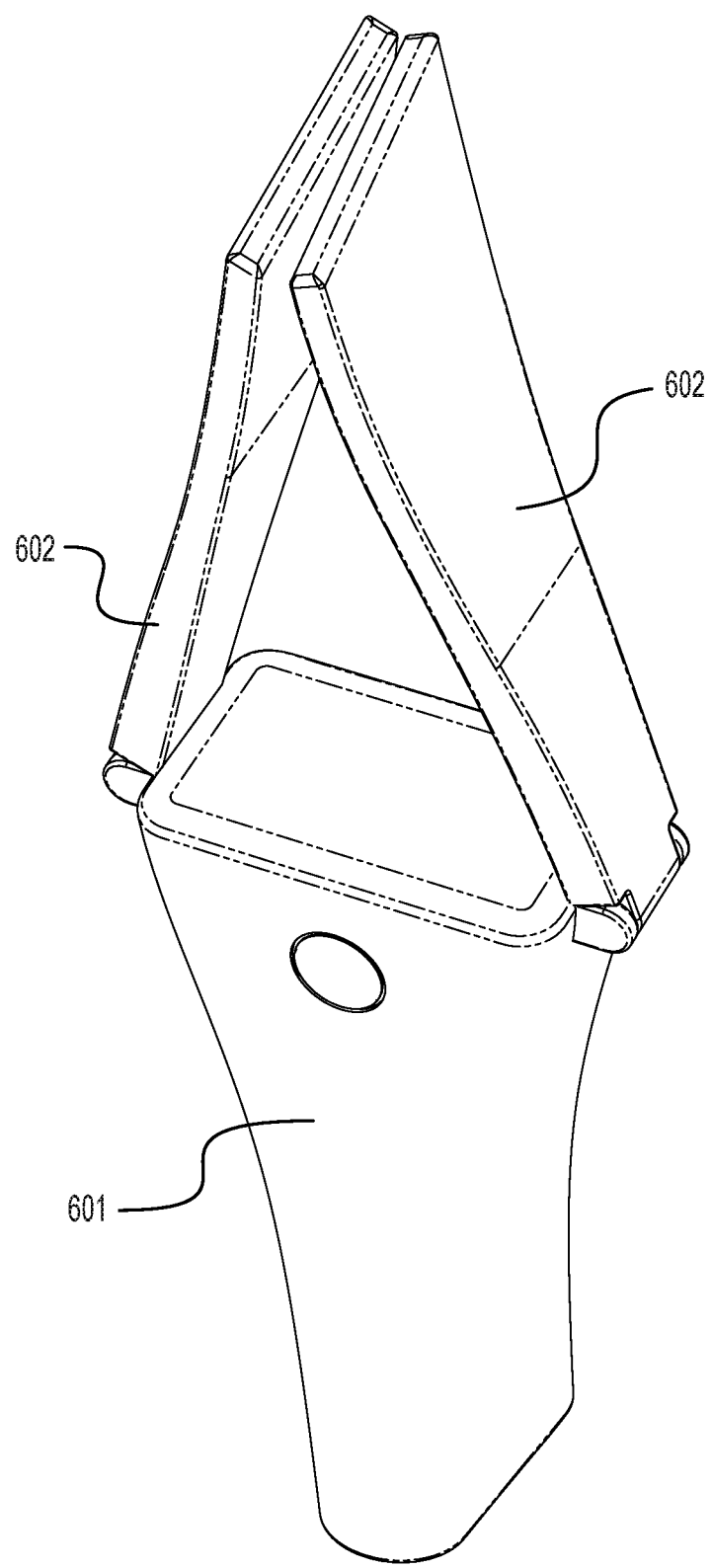

FIG. 10C shows the device with wings 602 in the 90 degree position, able to be placed on the lap of the user with the body of the device extending below the legs of the user, facing towards the drain hole of the toilet bowl. FIG. 10D shows the device with wings 602 in the 180 degree position, where it can be held by the hands of the user.

Figure 10E:
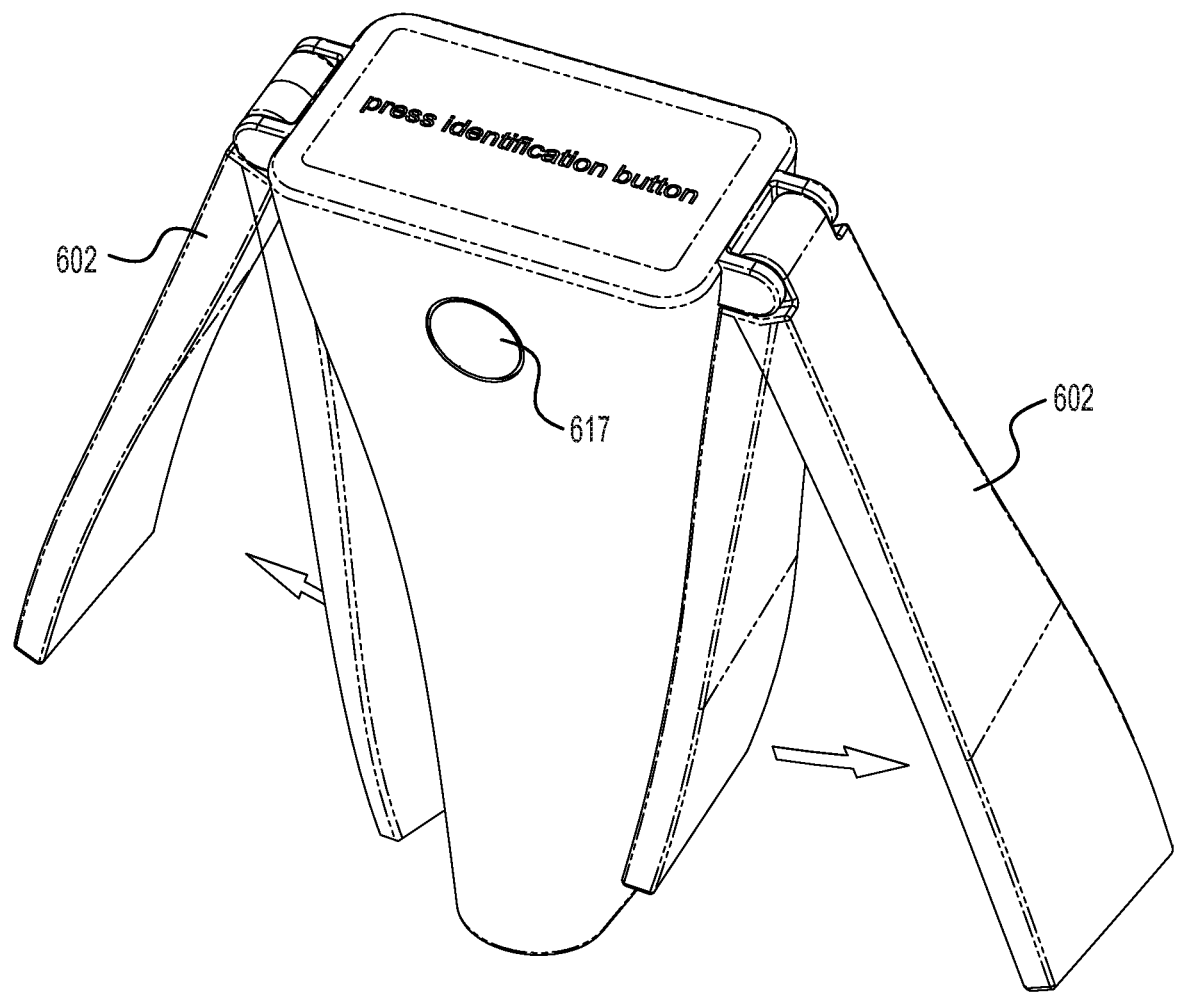
Figure 10G:
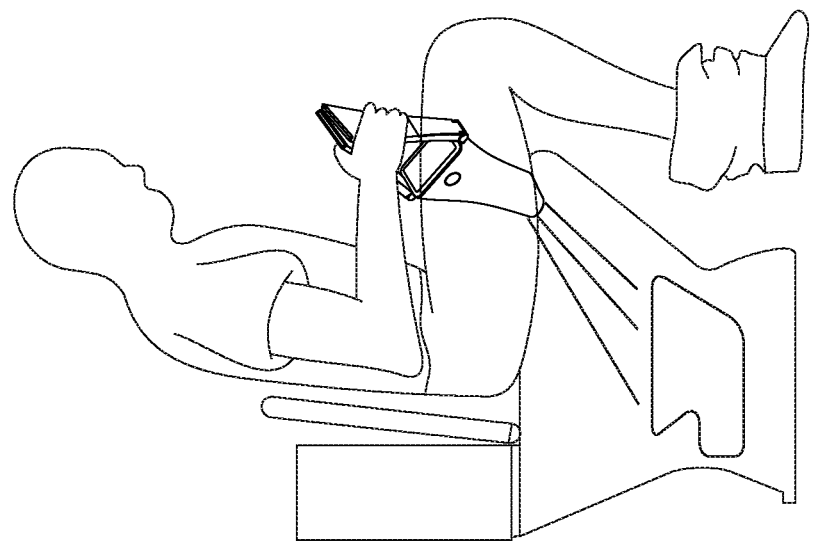
Figure 10F:
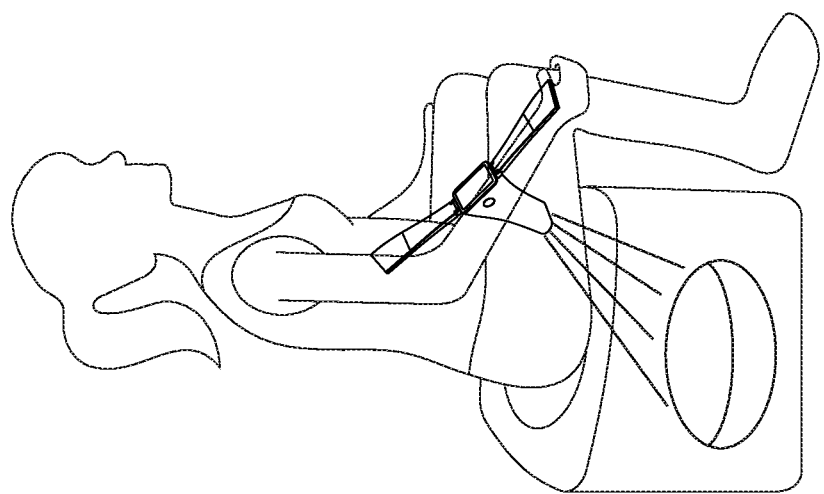
Figure 10H:
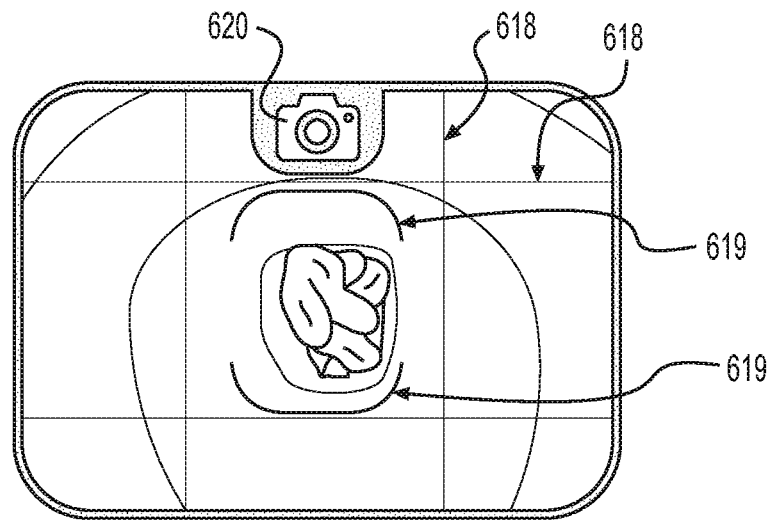
Figure 10I:
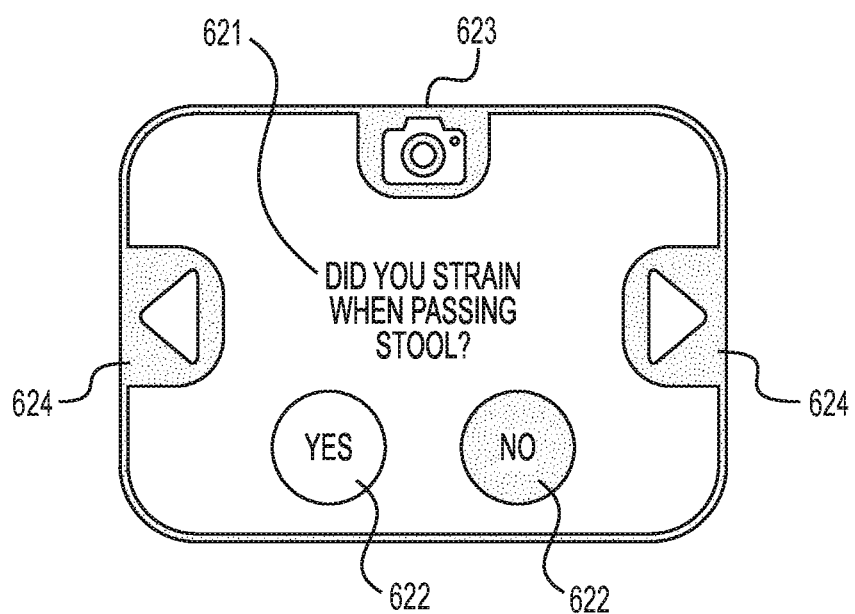

FIGS. 10E-I show the steps involved in turning on and using the device. FIG. 10E shows wings 602 being moved upwards from a down position, which is also a sleeping state meant to conserve battery power, towards a 90 degree position, which awakens the device and prompts the user to identify themselves through fingerprint sensor 617. FIG. 10F shows the device in use with wings 602 placed in a 90 degree position resting on the lap of a female user. FIG. 10G shows the device in use with wings 602 placed in a 180 degree position held in the hands of a male user. FIG. 10H shows a camera viewfinder on the top area of the device with guiding elements 618 and 619 that help the user position the device correctly and manually initiate image captures 620. Sound from 614 or haptic feedback from 615 is used to inform the user after a single or series of images are captured. FIG. 10I shows a question 621 that includes an area for answers 622, a way to capture additional images 623, in case the user needs to relieve himself or herself again, and a way to move forward or backward to different screens 624. Questions or questionnaires that are displayed to the user can be customized about topics such as urgency, satisfaction, pain, and difficulty of defecation and/or urination which are related to specific diseases or symptoms being tracked.

The device may also be used with or without added chemicals that manipulate the chemical matter in and on biological cells in the excreta, with which may be useful e.g., in detecting the presence of or quantifying blood which may be associated with conditions such as hemorrhoids, ulcerative colitis, colorectal cancer, Crohn's disease, urinary tract infections, and bladder cancer. Such chemicals may be a combination of reagents, buffers, oxidizers or other chemical agents may be liquid or deposited on a substrate that are dispensed into the toilet bowl before defecating or urinating in order to optically display changes in color versus the substrate or provide a photoluminescent glow that can be detected by the sensor 613. An example of such a substrate and color-based blood detection system approved by the US Food and Drug Administration for use with colorectal cancer screening is EZ Detect (Biomerica, Inc., Irvine, Calif., USA).

Figure 11B:
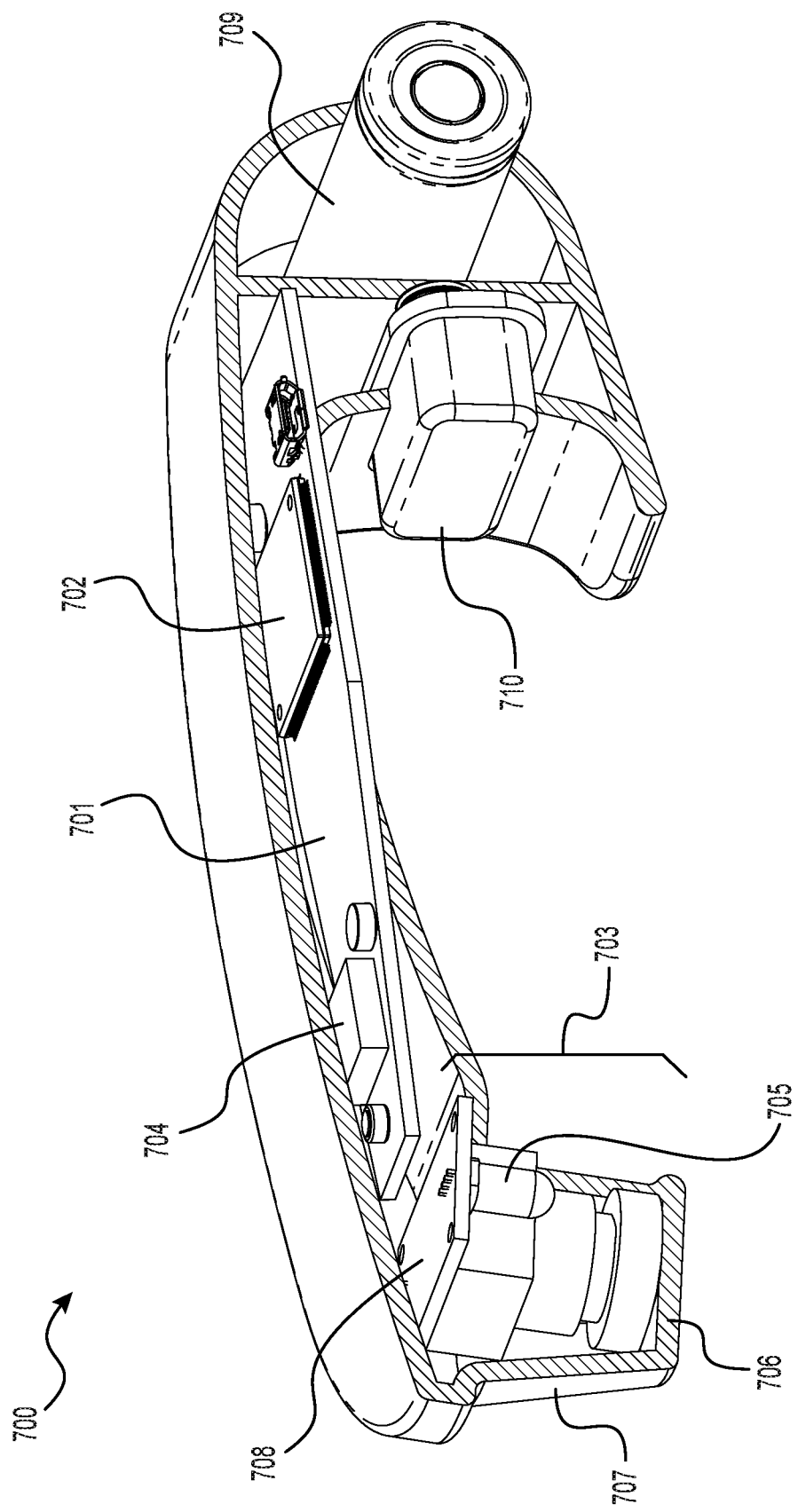

FIG. 11A shows an alternative embodiment of the portable device 700 installed on top of a toilet seat 232. The device can be successfully fitted in various positions around the circumference of the seat due to the conformity of features shown in FIGS. 11B-D.

FIG. 11B shows the components of the device in FIG. 11A. There is a printed circuit board assembly 701, module chip 702, image sensor assembly 703, which, in these embodiments, comprise the light source and CMOS sensor, and storage 704. On the toilet bowl interior side, there is an image sensor comprising an electromagnetic radiation source 705 providing light at various spectra into the toilet bowl, a lens 706 with low distortion that may be made of hydrophobic and/or antibacterial material that allows passage of light in the visible, near-infrared and ultraviolet spectrum, and a housing 707. The sensor 708 may also be a thermographic array comprised of focal plane arrays that respond to longer wavelengths (mid- and long-wavelength infrared). On the toilet bowl anterior side there is a battery 709 and a spring-loaded feature 710 shown in uncompressed position, that adapts to multiple seat widths to securely hold the device in place yet allows for easy and rapid removal by user.

Figure 11C:
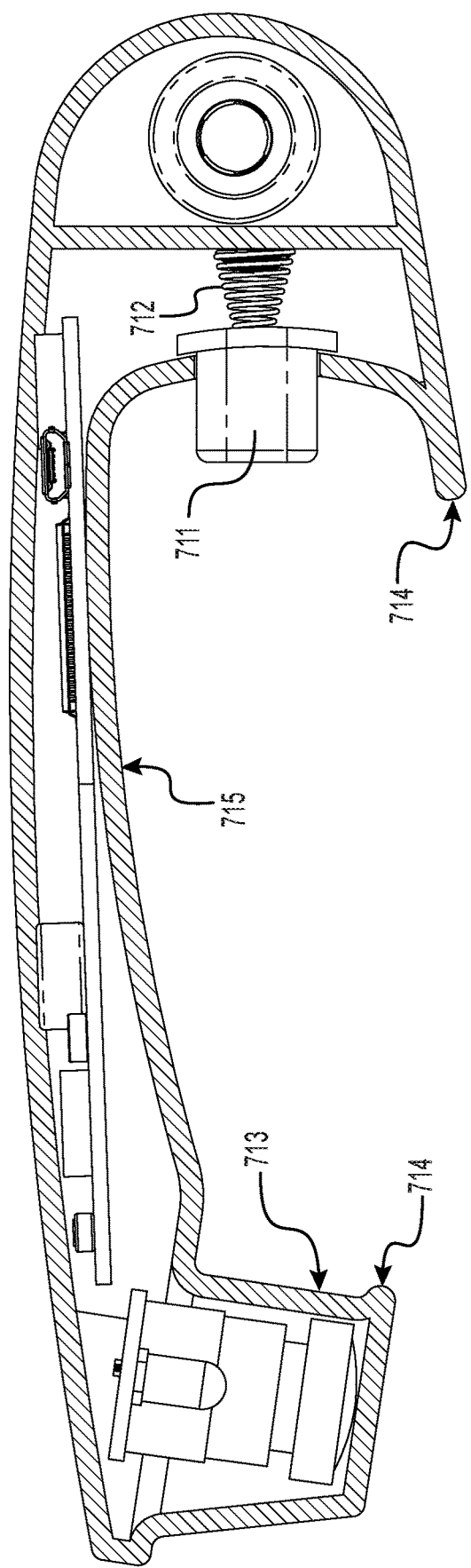
Figure 11D:
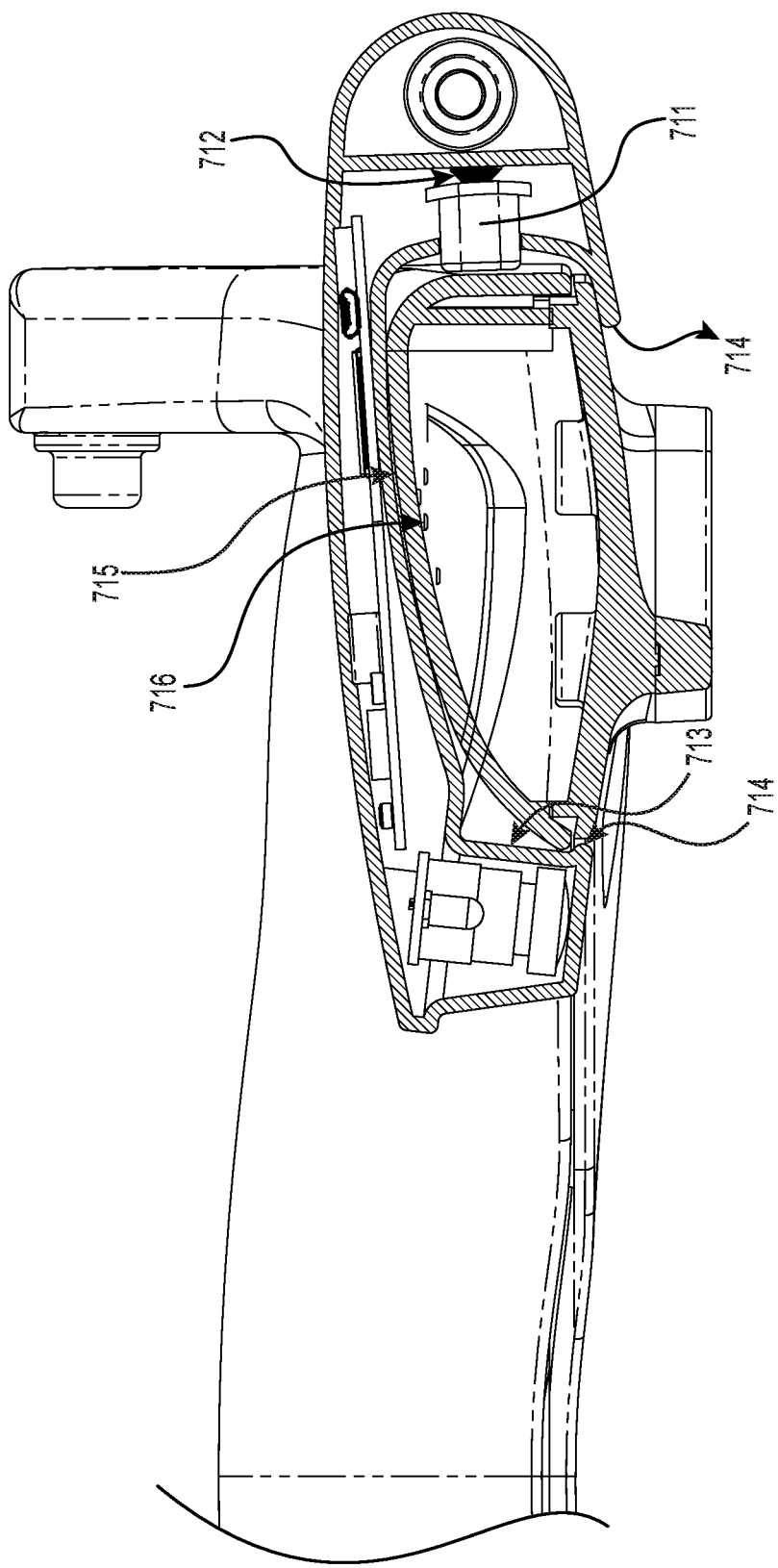

FIGS. 11C and 11D show section views that identify the features that allow the device shown in FIG. 11A to adapt to different widths and thicknesses of toilet seats. Sliding plunger 711 is a shown in uncompressed and compressed position, backed by spring 712 that applies pressure to the outside of a toilet seat 716 to provide a constant force against surface 713 to hold the device in place. Features 714 serve to resist upward force to keep device in place; feature 715 is positioned on the top of the toilet seat 716 to resist downward force.

Figure 12A:
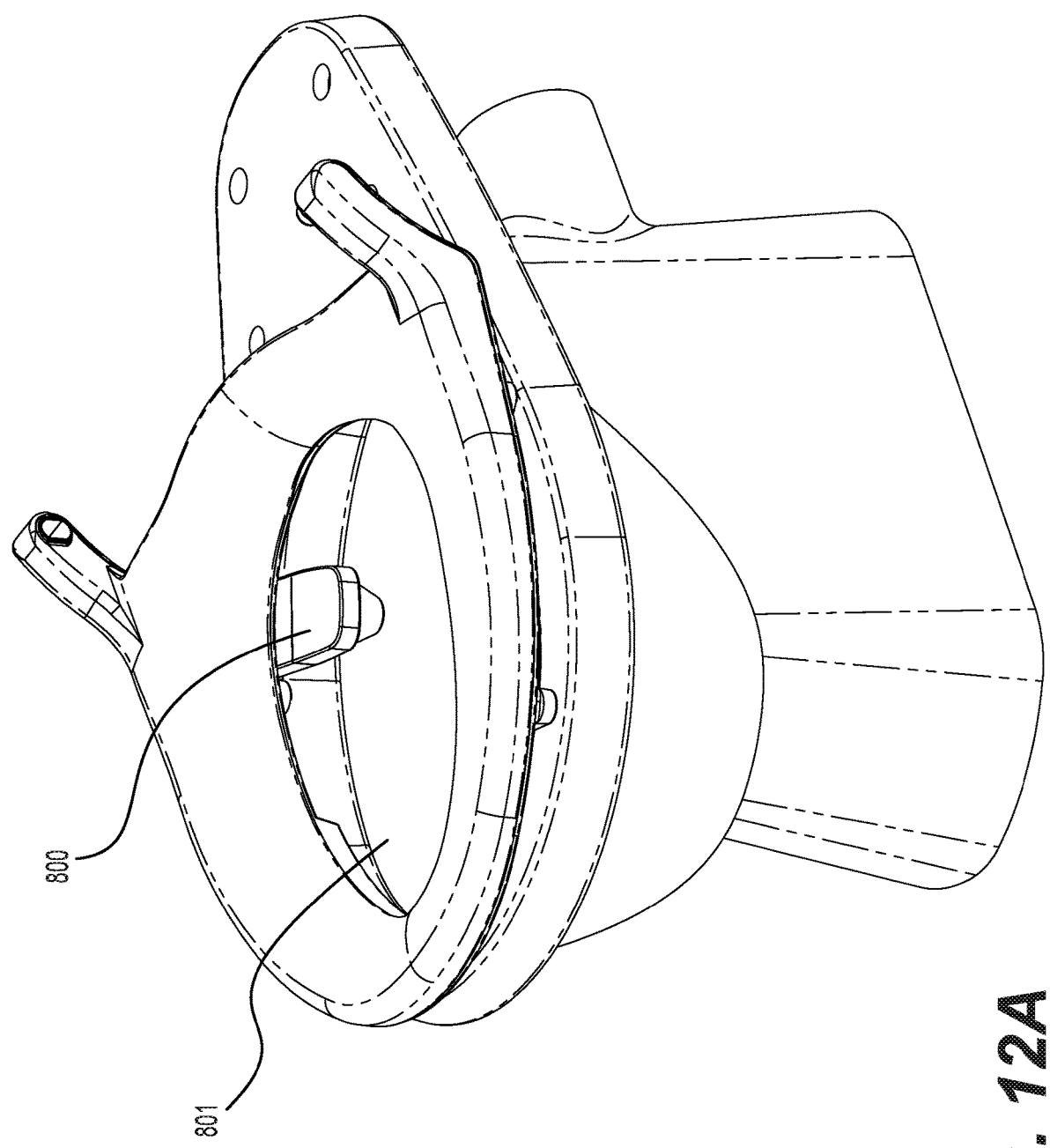
FIGS. 12A-12C illustrate an embodiment of a device of the present invention that fits between the bottom of a toilet seat and the toilet bowl rim.

FIG. 12A shows an alternative embodiment of device 800 in an in-use position installed below a toilet seat 716, above the toilet bowl 801 with the optical head able to be manually rotated for orientation to the excreta in the bowl.

Figure 12B:
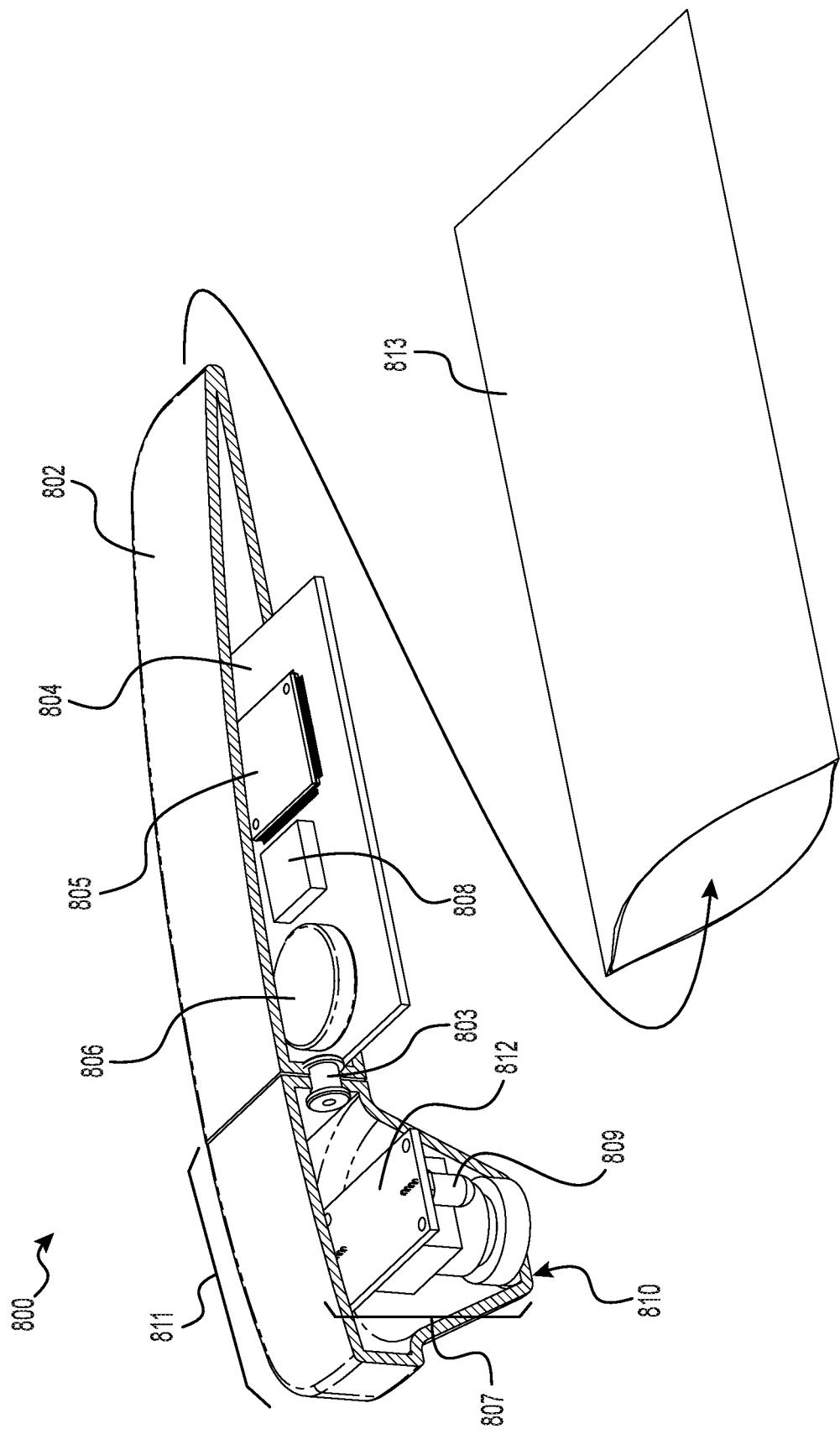

FIG. 12B shows device 800 of FIG. 12A comprised of an optical head positioned above the toilet bowl and an angled body intended to fit underneath a closed toilet seat, above the bowl rim and that has a tapered design 802 such that it can adapt to various height clearances between the top of a toilet bowl and bottom of a toilet seat. Design 802 is molded or covered by a conformal elastomeric material, which may also be antimicrobial, to provide grip to aid in retainment. Additionally, rotating feature 803 allows the optical head to be positioned for optimal alignment to the excreta in the toilet bowl. Internally, there is a printed circuit board assembly 804, module chip 805, battery 806, image sensor assembly 807, and storage 808. On the toilet bowl interior side, there is an image sensor comprising a light source 809 providing light at various spectra into the toilet bowl, a lens 810 with low distortion that may be made of hydrophobic material that allows passage of light in the visible, near-infrared and ultraviolet spectrum, a housing 811 for the image sensor assembly, and a CMOS sensor 812. Sensor 812 may also be a thermographic array comprised of focal plane arrays that respond to longer wavelengths (mid- and long-wavelength infrared). When device is used on potentially unclean toilets, a flushable sanitary bag 813 may be used to protect device 800 from direct contact with the toilet bowl rim and toilet seat.

Figure 12C:
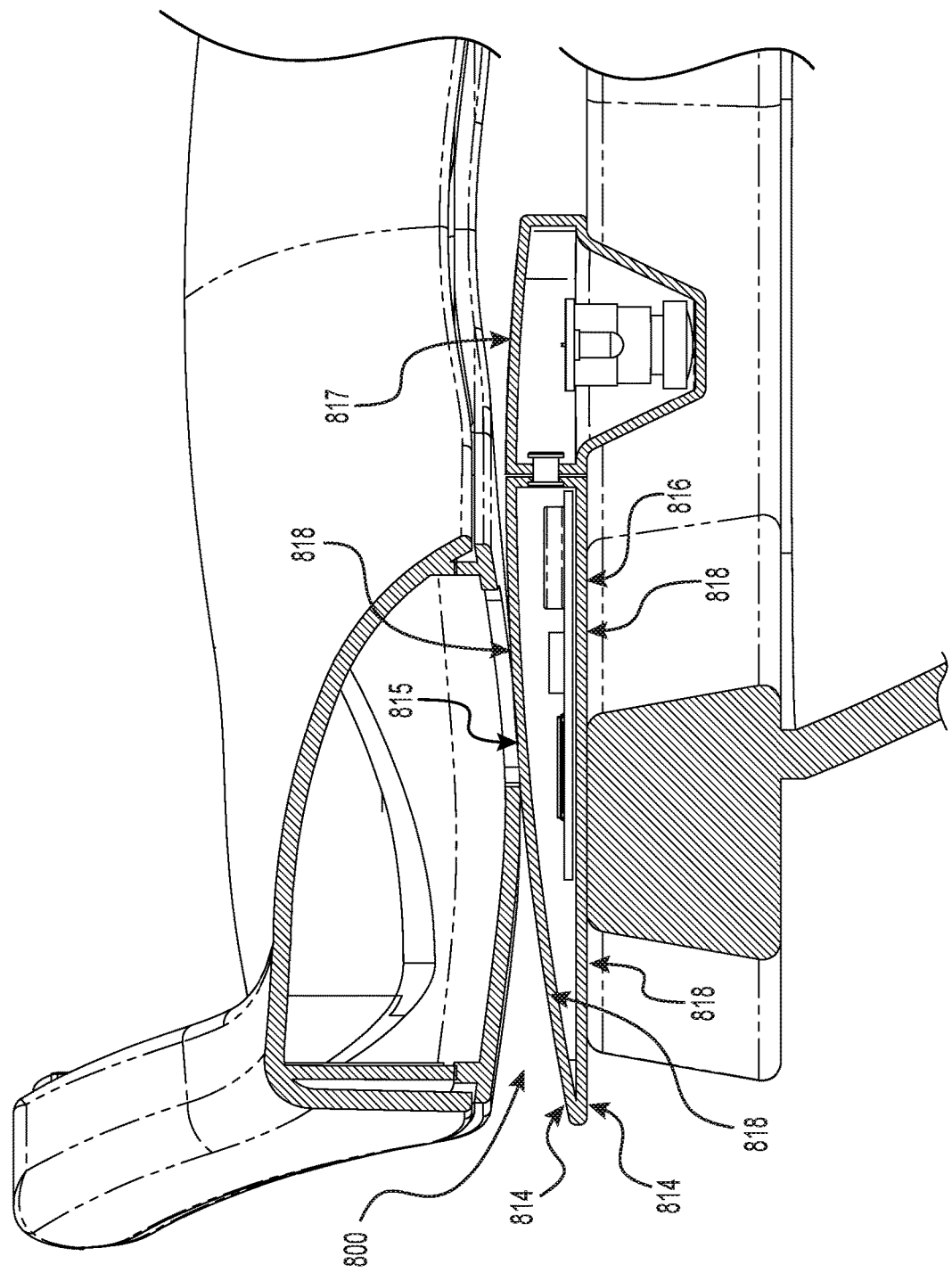

FIG. 12C shows device 800 of FIG. 12A utilizing design 802 wedge configuration 814 to fit securely between the bottom of a toilet seat 815 and the top of the toilet bowl rim 816. Optical head 817 is shown over toilet bowl. The wedge shape is covered by a sanitary bag all around surfaces shown in 818 to provide sufficient barrier from allowing device to touch toilet seat 815 or toilet bowl rim 816.

The embodiments described herein are not narrowly limited to the use of any particular power source. Thus, any of these embodiments may use mains electricity, electric batteries, solar power, etc.

In most embodiments, the device and/or system of the present invention further comprises a data storage and/or transmittal unit that stores and/or transmits data from the sensor via wireless, optical or wired communications to a computing unit, which analyzes data from the sensor.

Figure 13:
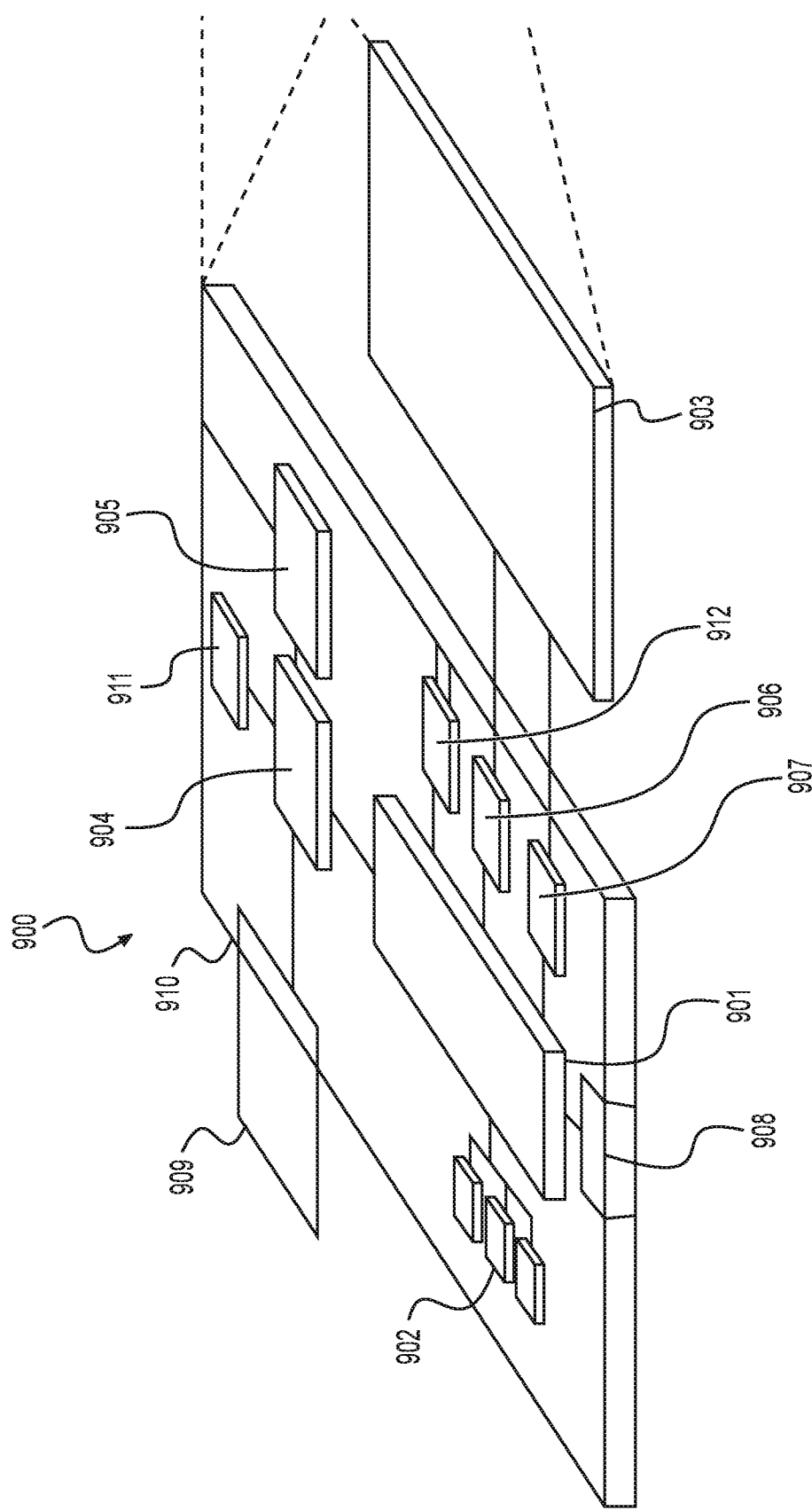
FIG. 13 illustrates an example of a generic computing device that may be used to store, transmit and process data from devices of the present invention.

FIG. 13 shows an example of a generic computing device 900, that may be used with the techniques described in this disclosure. In various embodiments, any or all of the components featured therein, and the functions performed thereby, can be incorporated into any of the devices described above.

Computing device 900 includes a processor 901, memory 902, an input/output device such as a display 903, a communication interface 904, and a transceiver 905, among other components. The computing device 900 may also be provided with a storage device, such as a microdrive or other device, to provide additional storage. Each of the components 900, 901, 902, 903, 904, and 905, are interconnected using various buses, and several of the components may be mounted on a common motherboard or in other manners as appropriate.

The processor 901 can execute instructions within the computing device 900, including instructions stored in the memory 902. The processor may be implemented as a chipset of chips that include separate and multiple analog and digital processors. The processor may provide, for example, for coordination of the other components of the computing device 900, such as control of user interfaces, applications run by computing device 900, and wireless communication by computing device 900.

Processor 901 may communicate with a user through control interface 906 and display interface 907 coupled to a display 903. The display 903 may be, for example, a Thin-Film-Transistor Liquid Crystal Display (TFT LCD) or an Organic Light Emitting Diode (OLED) display, or other appropriate display technology. The display interface 907 may comprise appropriate circuitry for driving the display 903 to present graphical and other information to a user. The control interface 906 may receive commands from a user and convert them for submission to the processor 901. In addition, an external interface 908 may be provided in communication with processor 901, to enable near area communication of computing device 900 with other devices. External interface 908 may provide, for example, for wired communication in some implementations, or for wireless communication in other implementations, and multiple interfaces may also be used.

The memory 902 stores information within the computing device 900. The memory 902 can be implemented as one or more of a computer-readable medium or media, a volatile memory unit or units, or a non-volatile memory unit or units. Expansion memory 909 may also be provided and connected to computing device 900 through expansion interface 910, which may include, for example, a SIMM (Single In Line Memory Module) card interface. Such expansion memory 909 may provide extra storage space for computing device 900 or may also store applications or other information for computing device 900. Specifically, expansion memory 909 may include instructions to carry out or supplement the processes described above and may also include secure information. Thus, for example, expansion memory 909 may be provided as a security module for computing device 900 and may be programmed with instructions that permit secure use of computing device 900. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 902, expansion memory 909, memory on processor 901, or a propagated signal that may be received, for example, over transceiver 905 or external interface 908.

Computing device 900 may communicate wirelessly through communication interface 904, which may include digital signal processing circuitry where necessary. Communication interface 904 may in some cases be a cellular modem. Communication interface 904 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1268. In addition, short-range communication may occur, such as using a Bluetooth, WiFi, or other such transceiver (not shown). In addition, GPS (Global Positioning System) receiver module 911 may provide additional navigation- and location-related wireless data to computing device 900, which may be used as appropriate by applications running on computing device 900.

Computing device 900 may also communicate audibly using audio codec 912, which may receive spoken information from a user and convert it to usable digital information. Audio codec 912 may likewise generate audible sound for a user, such as through a speaker, e.g., in a handset of computing device 900. Such sound may include sound from voice telephone calls, may include recorded sound (e.g., voice messages, music files, etc.) and may also include sound generated by applications operating on computing device 900.

The computing device 900 may be implemented in a number of different forms.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatuses, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language resource), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer.

Generally, a processor will receive instructions and data from a read-only memory or a random access memory or both. The essential elements of a computer are a processor for performing actions in accordance with instructions and one or more memory devices for storing instructions and data.

Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending resources to and receiving resources from a device that is used by the user; for example, by sending web pages to a web browser on a user's client device in response to requests received from the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

FIG. 14 is a block diagram that shows an example communications network architecture, devices and components, including representations of communication circuitry that may be incorporated in the example biometric monitoring devices according to at least certain embodiments of the present inventions; notably, the communication circuitry may implement or employ any form of communications (for example, wireless, optical, or wired) and/or protocol (for example, standard or proprietary) now known or later developed, all forms of communications and protocols are intended to fall within the scope of the present inventions (for example, Bluetooth, ANT, WLAN, Wi-Fi, power-line networking, all types and forms of Internet based communications, and/or SMS). Large files can be distributed using a peer-to-peer, distributed file sharing protocol which both increases scalability of the networked system's throughput as more nodes are added and adds security due to finger-printing for data integrity validation, inter-node consensus, and cryptographic shared secrets exchanged as an intrinsic aspect of the protocol. In some cases, an encrypted virtual private network is utilized to provide an extra level of security for all communications, but specifically administrative, maintenance & metric-gathering functions.

In the non-portable image sensor embodiments, before the image classification takes place, the images are conditioned for the classification. The unit takes several non-sample images (baseline images) during the day for calibration. Once the user's presence is detected, the unit can capture multiple images per second. Each image is then assessed for motion. To that end, a Harris & Stephens corner detector or similar is used to find corners in each image. The detected corners for each image are then assessed for motion by comparing a block of pixels around the corner of the current image with the next one in sequence using a motion detector like the Sum of Absolute Differences (SAD) processing. The number of flows above a set displacement threshold are then counted. If flows are counted above a set threshold, the image is deemed to be suboptimal and removed from further processing. The objective of this step is to limit the classification to the images that have a stationary sample. Depending on the analysis objective the image is then analyzed for indicative features.

In order to adapt to different toilets (including unique shapes, cleaning agents, water color conditions, material and porcelain colors) and lighting conditions, a baseline model of the empty toilet bowl may be obtained from the baseline images. To that extent, a training period of sample images are taken during a training period when no excreta is in the toilet bowl. These baseline images are taken with and without lighting to develop a robust background model that generates moving-average baselines. The background can be eliminated from the detection by frame differencing, a Gaussian mixture model for each pixel, or mean filter for each pixel. In frame differencing, the values of consecutive images without the sample are subtracted from the pixel values of the image with the sample. In the case of a Gaussian Mixture Model, a confidence band for the value of each pixel for the background is developed. As part of pre-processing, pixels that fall within a confidence interval of the modelled mixture are ignored. In case of the mean filter, an arithmetic mean of each pixel value is computed from images that do not contain the sample. This value is subtracted from the pixels of images that contain the sample. All pixels with a threshold close to zero are ignored from the classification, including glare spots and static artifacts that are specific to the environment. Furthermore, to be invariant to lighting changes histogram equalization is performed. This procedure improves contrast in the image and makes the classification robust across different lighting condition. Once defecation and/or urination is complete, which is detected through software-based image detection, the sample collection is disengaged and the images are processed locally or sent through access point 30 to networked computing resources in a cloud computing environment 50. Locally or remotely through memory 51 and processor 52 the images are then analyzed.

Figure 15A:
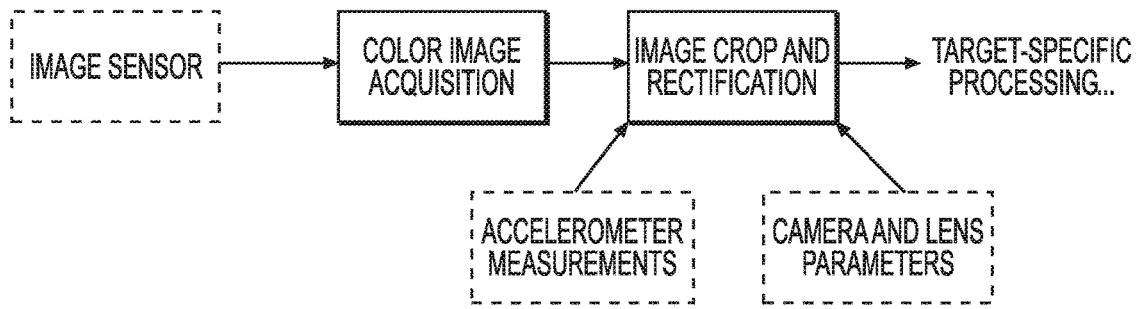

FIG. 15A is an image classification method for the portable device 600 that takes place after the user is identified, seated on the toilet and then points the device into the toilet bowl right before or during defecation and/or urination. As soon as the sample imaging is initiated, the light source is turned on, the application processor samples the image sensor continuously for frames, and the pan, tilt, and rotation angles are measured for each image captured from image sensor 613. The electromagnetic radiation source 611 projects light of light at various spectra into the toilet bowl. The three-axis accelerometer sampling the pan, tilt, and rotation angles of the unit can be a MEMS-based (such as the Invensense MPU-60x0) or a solid-state accelerometer. The image sensor is a color CCD or a CMOS-based image sensor. Further, the optical stack comprises a non-wide-angle lens (<90 degrees FOV). That sensor and lens combination results in low image distortion. The sensor has a minimum resolution of least 500×500 pixels. The frames and angles are sampled at rates in excess of 2 frames per second and saved locally on the device until the sample collection is disengaged.

Once defecation and/or urination is complete, which is detected through software-based image detection, sound detection, and/or the possible completion of questions such as those shown in FIG. 10I and/or readying the unit for transport, the sample collection is disengaged and the images are processed locally or sent through access point 40 to networked computing resources in a cloud computing environment 50. Locally or remotely through memory 51 and processor 52 the images are then analyzed.

In device 600 of the present invention (FIG. 10), the first step of the image processing is to rectify the images planar to the sample surface. As such the sampled pan, tilt, and rotation angles as well as the intrinsic camera parameters are used to compute an affine transformation of the image to the planar sample for each image. The images are then individually transformed to the perspective of the planar sample. The locations of known glare reflections of the light fixture are blackened. Each image is then assessed for motion. Similarly to the stationary unit, a Harris & Stephens corner detector or similar is used to find corners in each image. The detected corners for each image are then assessed for motion by comparing a block of pixels around the corner of the current image with the next one in sequence using a motion detector like the SAD processing. The number of flows above a set displacement threshold are then counted. If flows are counted above a set threshold, the image is deemed to be suboptimal and removed from further processing. The objective of this step is to limit the classification to the images that have a stationary sample. Depending on the analysis objective the image is then analyzed for indicative features.

Figure 15B:
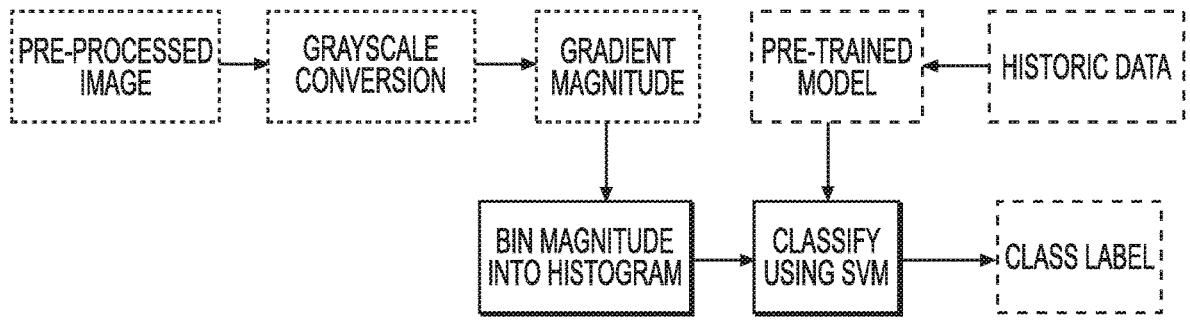

FIG. 15B is an image classification method for determining stool consistency. In embodiments where the image is captured in color, the first step is to convert the captured color image into a grayscale image. The gradient magnitude of the image is then computed using an operator such as Sobel-Feldman Operator. The gradient magnitudes are binned into a histogram of a fixed step size. Each image is encoded as features as a quantized histogram of gradients. These features are then fed into a pre-trained classifier, such as a support-vector machine (SVM), that classifies the feature into a label according to the Bristol stool scale, or other similar clinically accepted scales known in the art. The classifier that assigns the label has been trained to labeled sets of images. Each image of the training set was assigned a discrete label that has been assigned as ground truth. The training of the SVM minimizes classification errors against these ground truth labels. This classification method determines the stool consistency from a range of hard and lumpy to completely unformed and liquid, using standard clinical labels used in clinical studies to assess bowel consistency. However, instead of relying on patient self-reporting, this method automates or semi-automates the classification with objective images captured from the identified individual. An alternate method to determine stool consistency is to use a shallow neural network (NN). With more data, the NN will be more accurate since the first few layers of the neural network will, naturally with training, evolve into more accurate feature detectors than hand-crafted features such as histogram of gradients. The output of the NN is modeled as independent matrix functions for each desired class-label. The rectified linear unit on the individual output could be sigmoid function-like. The independent outputs are derived to "meta-class labels" such as healthy or unhealthy.

Figure 15C:
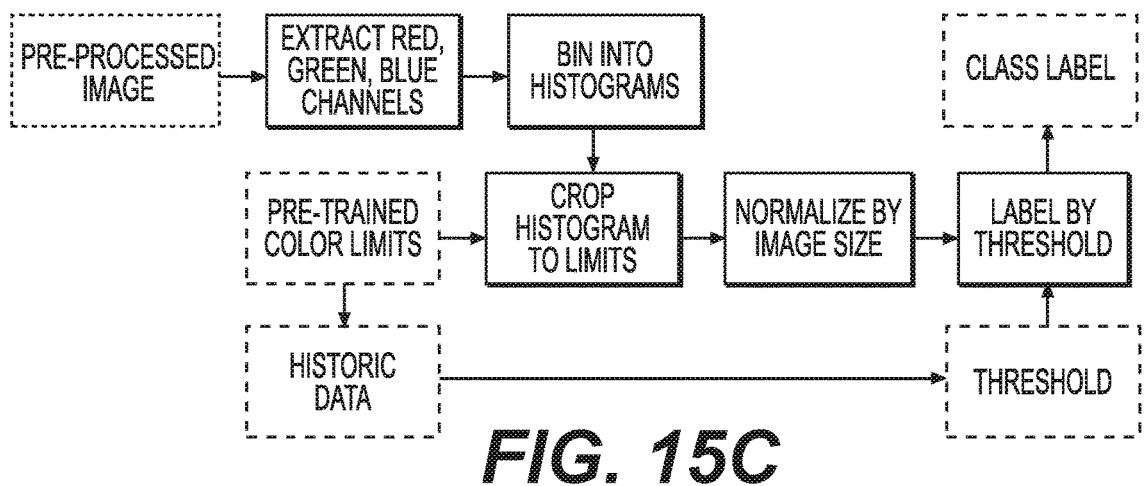

FIG. 15C is an image classification method for blood and urine colors. In pre-processing, the pixels that match a color distribution of stool, or known toilet fixtures, are blackened. From the remaining pixels a color histogram is computed for the red channel for blood, and the joint histogram of red and green for urine. The two histograms form the features for blood and urine classification respectively. From expert-labelled data, the limiting thresholds are obtained for each color channel for blood and urine and histograms for the color channels are cropped accordingly. Now the total count of values of the histogram is normalized to the total number of pixels in the remaining image. From the same historic data set, thresholds are obtained for the normalized count for each channel for true blood and urine samples respectively. Classification is then performed based on these thresholds. Alternatively, the normalized histograms of historic data are used to train an SVM. The pre-trained SVM provides a model to classify the histograms into known class labels. The features for blood and urine are then classified using pre-trained classifiers, such as SVM's. The SVM has been pre-trained with features from expert-labelled images for the desired class-labels. For computational efficiency SVMs are trained to classify the sample into categories. The images used to train the SVM are labelled by experts and features extracted in the same way as the sample for each type of analysis. Representative labels are indicated in FIG. 15D.

Figure 15E:
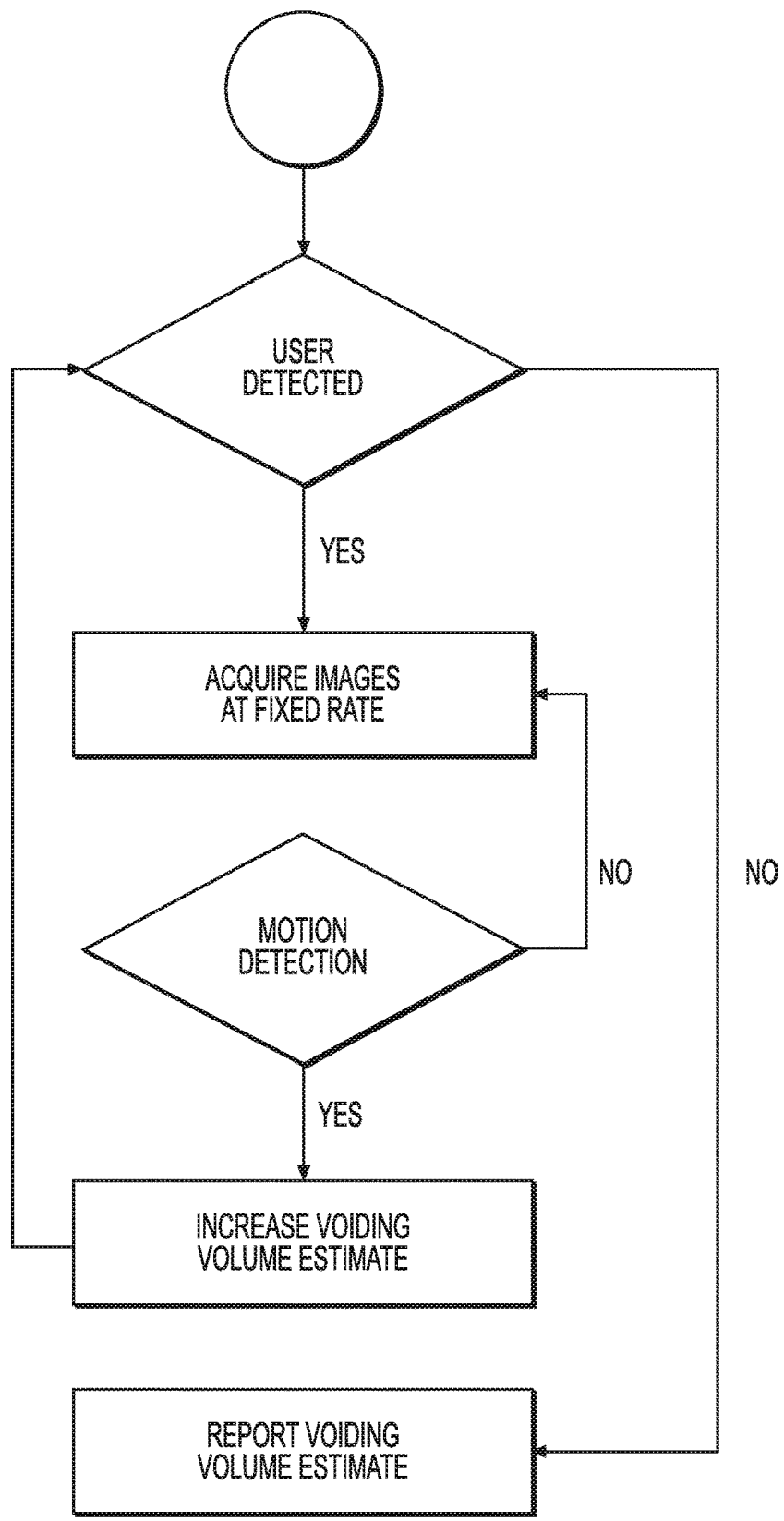
FIG. 15E shows the workflow for estimating the urine voiding volume of a person.

FIG. 15E shows the workflow for estimating the urine and stool voiding volume of a person. Temporal changes in water level are used to approximate voiding volume for urine and stool. The temporal change in level is a key indicator for density or porosity of the sample. The density estimate provides another input to a machine learning method to achieve a higher classification accuracy with respect to the Bristol stool scale or related methods, when combined with optical features. For each demographic and gender type the average constant voiding rate in milliliter per second can be specified. To approximate the voiding volume the start and the stop time of the voiding is performed using an image sensor. When the user voids, the water table inside the toilet exhibits motion. Optical motion sensing from pairs of consecutive frames flag if the person is still voiding. The sum of the inter-frame capture time of pairs of frames that exhibit motion is factored with the constant flow rate to model the voiding volume. Motion sensing approaches that pertain to this are background subtraction based on sum-of-absolute differences, motion sensing based on background subtraction of averages, and motion sensing based on background subtraction Gaussian Mixture models. Approaches that do not rely on a background model can also be used, such as thresholding a sum-of-absolute differences of pairs of frames.

To further improve the accuracy of the system the estimation of the voiding volume can be guarded by user detection using other means, such as a capacitive sensor capable of detecting when a user sits on the toilet seat or an ultrasonic sensor capable of detecting a standing user in front of the toilet, for example a male urinating standing up. This guard of the estimation process allows for excluding false sources of motion, and also resets the volume estimate across different users and periods of voiding.

The image classification methods and systems presented can be applied to obtain results from tests that may be performed in a toilet setting involving colorimetric changes. These include urine test strips, lateral flow tests or immunochromatographic assays, or other currently available or future tests where the precise measurement of color changes can be used to obtain quantitative or semi-quantitative results.

Information may also be interactively provided on a personal mobile device 60, which may be a smartphone or connected device worn on the body such as a wristwatch. After data is stored, analysis may also be conducted through human review, such as verifying flagged images or using information such as weight, body composition, stool consistency, stool frequency, urine color, voiding volume, urine frequency, and presence of visible blood to make a recommendation or provide an alert. In non-portable embodiments of the image sensor device, controlling the parameters and geometry of the lighting and imagers means that the system does not have to account for perspective distortion as a mobile camera would. Further, the fixed setting provides the opportunity to add polarization and wavelength filters to the imagers to limit the ingested light to a spectrum that shows the features needed for the classification more profoundly. By using polarization lenses effects of glare and unwanted reflections can be mitigated that provides a significant noise reduction and improves the overall quality of the classifiable features.

Figure 16:
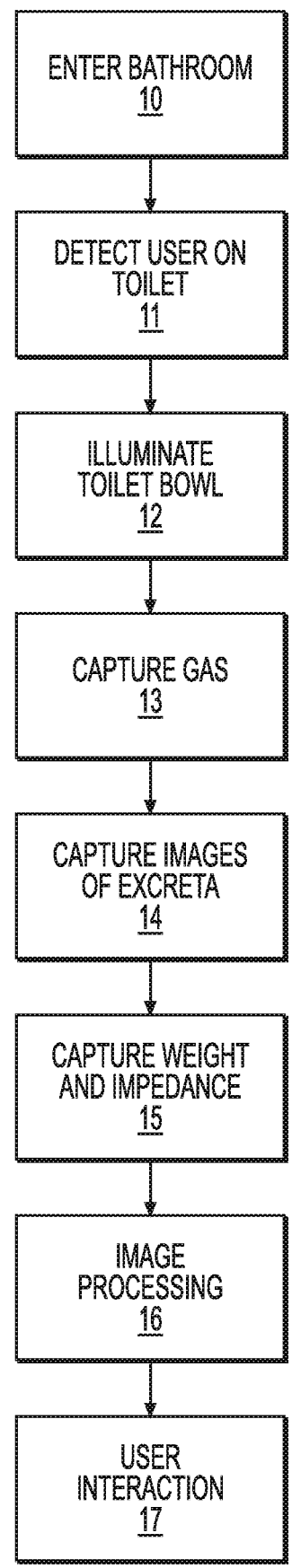
FIG. 16 is a block diagram that shows an exemplary set of steps taken by the user, devices, software, and/or user interfaces during use of the devices of the present invention.

In other embodiments, a method of determining a physiological parameter of a user is provided. The method comprises expelling a material into the bowl of a toilet in the presence of the above biomonitoring device. FIG. 16 shows a typical workflow for these methods.

REFERENCES

Gruber et al. (2016). Gas monitoring during a glucose challenge by a combined PTR-QMS/GCxGC-TOFMS approach for the verification of potential volatile biomarkers. Journal of breath research. 10:036003.

Janssen et al. (2000) Estimation of skeletal muscle mass by bioelectrical impedance analysis. Journal of Applied Physiology 89:465-471.

Kushner (1992). Bioelectrical impedance analysis: a review of principles and applications. Journal of the American College of Nutrition 11:199-209.

Kushner and Schoeller (1986). Estimation of total body water by bioelectrical impedance analysis. American Journal of Clinical Nutrition 44:417-424.

Zheng et al. (2011) The footprints of gut microbial-mammalian co-metabolism. Journal of proteome research. 10:5512-22.

U.S. Pat. No. 4,697,656.
U.S. Pat. No. 6,077,222.
U.S. Pat. No. 9,416,524.
U.S. Pat. No. 9,592,034.
U.S. Pat. No. 9,595,185.
U.S. Pat. No. 9,671,343.
U.S. Pat. No. 9,737,181.
U.S. Pat. No. 9,755,586.
U.S. Pat. No. 9,757,097.
U.S. Pat. No. 9,766,257.
U.S. Pat. No. 9,801,508.
U.S. Pat. No. 9,810,686.
U.S. Pat. No. 9,822,519.
U.S. Pat. No. 9,845,593.
U.S. Pat. No. 9,867,513.
U.S. Pat. No. 9,880,138.
US Patent Application Publication 2006/0155175.
US Patent Application Publication 2017/0135677.
US Patent Application Publication 2010/0170722.
US Patent Application Publication 2010/0205722.
US Patent Application Publication 2016/0374619.
US Patent Application Publication 2017/0198464.
US Patent Application Publication 2017/0198466.
US Patent Application Publication 2017/0198466.
US Patent Application Publication 2017/0204595.
US Patent Application Publication 2017/0251996.
US Patent Application Publication 2017/0254060.
US Patent Application Publication 2017/0254526.
US Patent Application Publication 2017/0322197.
US Patent Application Publication 2018/0000417.
US Patent Application Publication 2018/0020889.
US Patent Application Publication 2018/0020984.
US Patent Application Publication 2018/0052955.

In view of the above, it will be seen that several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A biomonitoring device that measures a parameter of a material expelled into a bowl of a toilet by a user, the device comprising
(i) an electromagnetic radiation source above the material, wherein the electromagnetic radiation source emits electromagnetic radiation into the bowl of the toilet, and
(ii) a sensor comprising a lens above the material that detects electromagnetic radiation or an analyte chemical in the bowl of the toilet,
wherein (i) and (ii) are behind a sitting portion of a seat of the toilet, and
wherein the lens is situated such that it does not change position, relative to the bowl of the toilet, when the seat of the toilet is lifted.

2. The device of claim 1, wherein the sensor is an image sensor comprising the lens.

3. The device of claim 2, wherein the sensor further comprises a complementary metal-oxide-semiconductor.

4. The device of claim 1, further comprising components for spectroscopic detection comprising a laser diode and a photodetector.

5. The device of claim 1, wherein the sensor detects an analyte chemical in the bowl.

6. The device of claim 1, further comprising a polarization filter.

7. The device of claim 1, further comprising a capacitive sensor that detects the presence of the user while seated on the seat of the toilet.

8. The device of claim 1, further comprising a data storage and/or transmittal unit that stores and/or transmits data from the sensor.

9. The device of claim 8, comprising a transmittal unit that transmits data via wireless, optical or wired communications to a computing unit.

10. The device of claim 9, wherein the device undergoes a training period where data is analyzed when no excreta is in the bowl, wherein the training period comprises taking baseline sample images when no excreta is in the bowl and obtaining a baseline model of the empty toilet bowl from the baseline images.

11. The device of claim 9, wherein the computing unit analyzes the data to determine stool consistency, presence of blood, urine color, urine voiding volume, weight, body composition, stool frequency, urine frequency, or any combination thereof.

12. The device of claim 1, further comprising a scale or footstool comprising a thin film pressure sensor that captures a weight of the user.

13. The device of claim 1, wherein the material is urine or feces.

14. The device of claim 1, further comprising a nozzle capable of dispensing a liquid into the bowl.

15. A biomonitoring device that measures a parameter of a material expelled into a bowl of a toilet by a user, the device comprising
(i) an electromagnetic radiation source above the material, wherein the electromagnetic radiation source emits electromagnetic radiation into the bowl of the toilet,
(ii) a sensor comprising a lens above the material that detects electromagnetic radiation or an analyte chemical in the bowl of the toilet, and
(iii) a transmittal unit that transmits data to a computing unit,
wherein the device undergoes a training period where data is analyzed when no excreta is in the bowl, wherein the training period comprises taking baseline sample images when no excreta is in the bowl and obtaining a baseline model of the empty toilet bowl from the baseline images.

16. The biomonitoring device of claim 15, wherein the lens is situated such that it does not change position, relative to the bowl of the toilet, when the seat of the toilet is lifted.

17. The biomonitoring device of claim 15, wherein (i) and (ii) are behind a sitting portion of a seat of the toilet.

18. The biomonitoring device of claim 15, further comprising a polarization filter.

* * * * *

(12) EX PARTE REEXAMINATION CERTIFICATE (12955th)
United States Patent
Kashyap et al.

(10) Number: US 11,298,112 C1
(45) Certificate Issued: Jul. 1, 2025

(54) BIOMONITORING DEVICES, METHODS, AND SYSTEMS FOR USE IN A BATHROOM SETTING

(71) Applicant: Toi Labs, Inc., San Francisco, CA (US)

(72) Inventors: Vikram Kashyap, San Francisco, CA (US); Kevin D. Simmons, San Francisco, CA (US); Thomas Reidemeister, Waterloo (CA); Benjamin K. Yaffe, San Francisco, CA (US); Rodolfo Camacho, San Francisco, CA (US)

(73) Assignee: TOI LABS, INC., San Francisco, CA (US)

Reexamination Request:
No. 90/019,567, Jul. 9, 2024

Reexamination Certificate for:
Patent No.: 11,298,112
Issued: Apr. 12, 2022
Appl. No.: 16/446,111
Filed: Jun. 19, 2019

Related U.S. Application Data

(63) Continuation of application No. 16/016,559, filed on Jun. 23, 2018, now Pat. No. 10,376,246, which is a continuation of application No. PCT/US2018/026618, filed on Apr. 6, 2018.

(60) Provisional application No. 62/482,912, filed on Apr. 7, 2017.

(51) Int. Cl.
*G01N 33/49* (2006.01)
*A61B 10/00* (2006.01)
*E03D 11/13* (2006.01)
*G01N 21/31* (2006.01)
*G01N 33/483* (2006.01)
*G01N 33/493* (2006.01)
*H04N 23/56* (2023.01)
*H04N 25/76* (2023.01)
*G01G 19/50* (2006.01)
*G01G 21/28* (2006.01)

(52) U.S. Cl.
CPC ........ *A61B 10/0038* (2013.01); *A61B 10/007* (2013.01); *E03D 11/13* (2013.01); *G01N 21/31* (2013.01); *G01N 33/4833* (2013.01); *G01N 33/49* (2013.01); *G01N 33/493* (2013.01); *H04N 23/56* (2023.01); *H04N 25/76* (2023.01); *A61B 2010/0083* (2013.01); *G01G 19/50* (2013.01); *G01G 21/28* (2013.01)

(58) Field of Classification Search
None
See application file for complete search history.

(56) References Cited

To view the complete listing of prior art documents cited during the proceeding for Reexamination Control Number 90/019,567, please refer to the USPTO's Patent Electronic System.

*Primary Examiner* — Deandra M Hughes

(57) ABSTRACT

Provided is a biomonitoring device that measures a parameter of a material expelled during use of a toilet by a user. Also provided is a biomonitoring mirror device that identifies a user, detects a febrile illness in a user, dispenses medications/supplements, connects to electrical device accessories in the bathroom, and provides an interactive user interface. Additionally provided is a system for measuring a parameter of a material expelled during use of a toilet by a user. Further provided is a method of determining a physiological parameter of a user.

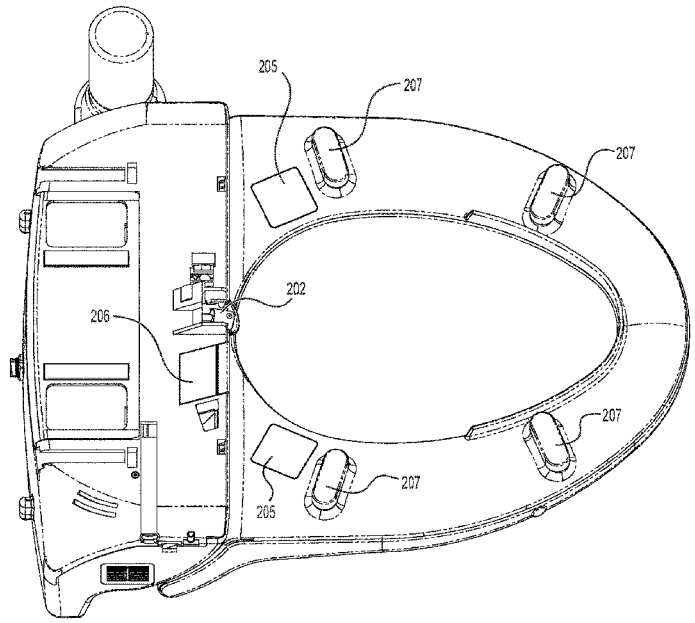

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 14, 15 and 17 are determined to be patentable as amended.

Claims 2-13, 16 and 18, dependent on an amended claim, are determined to be patentable.

New claim 19 is added and determined to be patentable.

1. A biomonitoring device that measures a parameter of a material expelled into a bowl of a toilet by a user, the device comprising:
    (i) an electromagnetic radiation source above the material, wherein the electromagnetic radiation source emits electromagnetic radiation into the bowl of the [toilet,] *toilet*; and
    (ii) a sensor comprising a lens above the material that detects electromagnetic radiation or an analyte chemical in the bowl of the [toilet,] *toilet;*
    wherein [(i)] *the electromagnetic radiation source* and [(ii)] *the sensor* are behind a sitting portion of a seat of the toilet, and
    wherein, the lens is *fixed with respect to the bowl and is* situated such that [it] *the lens* does not change position, relative to the bowl of the toilet, when the seat of the toilet is lifted.

14. The device of claim 1, further comprising a nozzle capable of dispensing a liquid into the bowl, *wherein the nozzle is positioned separately from the electromagnetic radiation source*.

15. A biomonitoring device that measures a parameter of a material expelled into a bowl of a toilet by a user, the device comprising:
    (i) an electromagnetic radiation source above the material, wherein the electromagnetic radiation source emits electromagnetic radiation into the bowl of the [toilet,] *toilet*;
    (ii) a sensor comprising a lens above the material that detects electromagnetic radiation or an analyte chemical in the bowl of the [toilet, and] *toilet; and*
    (iii) a transmittal unit that transmits data to a computing [unit,] *unit;*
    wherein the device undergoes a training period where data is analyzed when no excreta is in the bowl, wherein the training period comprises taking baseline sample images when no excreta is in the bowl and obtaining a baseline model of the empty toilet bowl from the baseline images*; and*
    *wherein the electromagnetic radiation source and the sensor are below a sitting portion of the seat of the toilet and wherein the lens is fixed with respect to the bowl.*

17. The biomonitoring device of claim 15, wherein [(i) and (ii)] *the electromagnetic radiation source and the sensor* are behind *and below* a sitting portion of a seat of the toilet.

19. *The device claim 1, wherein the electromagnetic radiation source and the sensor are behind and below a sitting portion of the seat of the toilet.*

\* \* \* \* \*